US008709384B2

(12) United States Patent
Reb

(10) Patent No.: US 8,709,384 B2
(45) Date of Patent: Apr. 29, 2014

(54) COMPOSITIONS AND METHODS USING MICROSPHERES AND NON-IONIC CONTRAST AGENTS

(75) Inventor: Philippe Reb, Chaumes en Brie (FR)

(73) Assignee: Biosphere Medical, S.A., South Jordan, UT (US)

( * ) Notice: Subject to any disclaimer, the term of this patent is extended or adjusted under 35 U.S.C. 154(b) by 0 days.

(21) Appl. No.: 13/435,520

(22) Filed: Mar. 30, 2012

(65) Prior Publication Data

US 2012/0189552 A1 Jul. 26, 2012

Related U.S. Application Data

(63) Continuation of application No. 11/430,789, filed on May 9, 2006, now Pat. No. 8,226,926.

(60) Provisional application No. 60/679,348, filed on May 9, 2005.

(51) Int. Cl.
*A61B 5/055* (2006.01)
*A61K 49/04* (2006.01)

(52) U.S. Cl.
USPC ....... 424/9.37; 424/9.36; 424/9.4; 424/9.452; 424/9.454

(58) Field of Classification Search
USPC ............... 424/1.11, 9.36, 422, 426, 489–490, 424/496, 497, 501, 9.37, 9.4, 9.452, 9.454
See application file for complete search history.

(56) References Cited

U.S. PATENT DOCUMENTS

| | | | |
|---|---|---|---|
| 3,673,125 A | 6/1972 | Takahashi et al. |
| 3,919,411 A | 11/1975 | Glass et al. |
| 4,192,784 A | 3/1980 | Brown et al. |
| 4,197,846 A | 4/1980 | Bucalo |
| 4,245,064 A | 1/1981 | Drobnik et al. |
| 4,268,495 A | 5/1981 | Muxfeldt et al. |
| 4,306,031 A | 12/1981 | Itagaki et al. |
| 4,314,032 A | 2/1982 | Murayama et al. |
| 4,320,040 A | 3/1982 | Fujita et al. |
| 4,350,773 A | 9/1982 | Itagaki et al. |
| 4,367,323 A | 1/1983 | Kitamura et al. |
| 4,413,070 A | 11/1983 | Rembaum |
| 4,452,916 A | 6/1984 | Boschetti et al. |
| 4,500,658 A | 2/1985 | Fox |
| 4,622,362 A | 11/1986 | Rembaum |
| 4,657,553 A | 4/1987 | Taylor |
| 4,680,171 A | 7/1987 | Shell |
| 4,803,075 A | 2/1989 | Wallace et al. |
| 4,816,397 A | 3/1989 | Boss et al. |
| 4,816,567 A | 3/1989 | Cabilly et al. |
| 4,863,972 A | 9/1989 | Itagaki et al. |
| 4,873,316 A | 10/1989 | Meade et al. |
| 4,999,188 A | 3/1991 | Solodovnik et al. |
| 5,007,940 A | 4/1991 | Berg |
| 5,028,332 A | 7/1991 | Ohnishi |
| 5,092,883 A | 3/1992 | Epply et al. |
| 5,106,876 A | 4/1992 | Kawamura |
| 5,114,577 A | 5/1992 | Kusano et al. |
| 5,116,742 A | 5/1992 | Cech et al. |
| 5,171,678 A | 12/1992 | Behr et al. |
| 5,186,922 A | 2/1993 | Shell et al. |
| 5,202,352 A | 4/1993 | Okada et al. |
| 5,298,570 A | 3/1994 | Tahara et al. |
| 5,312,617 A | 5/1994 | Unger et al. |
| 5,344,452 A | 9/1994 | Lemperle |
| 5,403,870 A | 4/1995 | Gross |
| 5,410,016 A | 4/1995 | Hubbell et al. |
| 5,451,406 A | 9/1995 | Lawlin et al. |
| 5,470,911 A | 11/1995 | Rhee et al. |
| 5,476,962 A | 12/1995 | Behr et al. |
| 5,550,187 A | 8/1996 | Rhee et al. |
| 5,550,188 A | 8/1996 | Rhee et al. |
| 5,554,659 A | 9/1996 | Rosenblatt |
| 5,571,182 A | 11/1996 | Ersek et al. |
| 5,578,709 A | 11/1996 | Woiszwillo |
| 5,583,162 A | 12/1996 | Li et al. |
| 5,593,990 A | 1/1997 | D'Amato |
| 5,616,745 A | 4/1997 | Behr et al. |
| 5,624,685 A | 4/1997 | Takahashi et al. |
| 5,629,327 A | 5/1997 | D'Amato |

(Continued)

FOREIGN PATENT DOCUMENTS

| | | |
|---|---|---|
| CA | 2248592 | 4/2000 |
| EP | 0256293 | 2/1988 |

(Continued)

OTHER PUBLICATIONS

International Search Report for PCT/EP2006/004334 dated Nov. 16, 2006.
Hori et al., 'Recent Advancement of Embolization Therapy'. Nichidoku Iho [Japanisch-Deutsche Medixinische Berichte], 40(1): 169-175, 1995.
Inaba et al., 'Arterial Embolization of Facial Arteriovenous Malformation with Super Absorbent Polymer Microsphere: A Case of Surgical Ligation of External Carotid Artery'. Intervent. Radiol. 11: 108-112, 1996.

(Continued)

*Primary Examiner* — Michael G Hartley
*Assistant Examiner* — Jagadishwar Samala
(74) *Attorney, Agent, or Firm* — Stoel Rives LLP

(57) ABSTRACT

The present invention relates to compositions and methods for treating diseases and disorders including cancer and various other angiogenic-dependent diseases, vascular malfunctions, arteriovenous malformations (AVM), hemorrhagic processes and treatment of pain, in particular tumor-related pain by drug delivery and/or therapeutic embolization using microspheres. More particularly the invention relates to microspheres containing non-ionic contrast agents, to compositions comprising these microspheres, as well as methods for preparing and using such compositions for embolization therapy. The invention further relates to compositions and methods using detectable microspheres for targeted drug delivery, irrespective of whether embolization is also needed.

15 Claims, No Drawings

(56) References Cited

U.S. PATENT DOCUMENTS

| | | |
|---|---|---|
| 5,633,001 A | 5/1997 | Agerup |
| 5,635,215 A | 6/1997 | Boschetti et al. |
| 5,639,872 A | 6/1997 | Robinson |
| 5,648,100 A | 7/1997 | Boschetti et al. |
| 5,653,922 A | 8/1997 | Li et al. |
| 5,654,006 A | 8/1997 | Fernandez et al. |
| 5,712,291 A | 1/1998 | D'Amato |
| 5,716,404 A | 2/1998 | Vacanti et al. |
| 5,716,981 A | 2/1998 | Hunter et al. |
| 5,752,974 A | 5/1998 | Rhee et al. |
| 5,760,097 A | 6/1998 | Li et al. |
| 5,785,977 A | 7/1998 | Briethbarth |
| 5,798,096 A | 8/1998 | Pavlyk |
| 5,823,198 A | 10/1998 | Jones et al. |
| 5,830,686 A | 11/1998 | Henderson |
| 5,853,698 A | 12/1998 | Straub et al. |
| 5,855,610 A | 1/1999 | Vacanti et al. |
| 5,863,957 A | 1/1999 | Li et al. |
| 5,871,726 A | 2/1999 | Henderson et al. |
| 5,891,470 A | 4/1999 | Rinaldi et al. |
| 5,894,022 A | 4/1999 | Ji et al. |
| 5,895,411 A | 4/1999 | Irie |
| 5,925,683 A | 7/1999 | Park |
| 5,932,248 A | 8/1999 | Chen et al. |
| 5,955,108 A | 9/1999 | Sutton et al. |
| 5,981,719 A | 11/1999 | Woiszwillo et al. |
| 5,985,177 A | 11/1999 | Yoshida et al. |
| 6,048,908 A | 4/2000 | Kitagawa |
| 6,060,530 A | 5/2000 | Chaouk et al. |
| 6,060,582 A | 5/2000 | Hubbell et al. |
| 6,083,484 A | 7/2000 | Lohrmann et al. |
| 6,086,863 A | 7/2000 | Ritter et al. |
| 6,090,800 A | 7/2000 | Unger et al. |
| 6,099,864 A | 8/2000 | Morrison et al. |
| 6,100,306 A | 8/2000 | Li et al. |
| 6,160,025 A | 12/2000 | Slaikeu et al. |
| 6,165,193 A | 12/2000 | Greene, Jr. et al. |
| 6,191,193 B1 | 2/2001 | Lee et al. |
| 6,218,440 B1 | 4/2001 | Kitagawa |
| 6,224,794 B1 | 5/2001 | Amsden et al. |
| 6,242,512 B1 | 6/2001 | Figge et al. |
| 6,290,729 B1 | 9/2001 | Stepian et al. |
| 6,306,922 B1 | 10/2001 | Hubbell et al. |
| 6,316,011 B1 | 11/2001 | Ron et al. |
| 6,335,028 B1 | 1/2002 | Vogel et al. |
| 6,364,823 B1 | 4/2002 | Garibaldi et al. |
| 6,436,424 B1 | 8/2002 | Vogel |
| 6,488,952 B1 | 12/2002 | Kennedy et al. |
| 6,500,190 B2 | 12/2002 | Greene, Jr. et al. |
| 6,506,411 B2 | 1/2003 | Hunter et al. |
| 6,537,569 B2 | 3/2003 | Cruise |
| 6,548,047 B1 | 4/2003 | Unger |
| 6,562,317 B2 | 5/2003 | Greff et al. |
| 6,565,885 B1 | 5/2003 | Tarara et al. |
| 6,602,975 B2 | 8/2003 | Hubbell et al. |
| 6,652,883 B2 | 11/2003 | Goupil et al. |
| 6,660,301 B1 | 12/2003 | Vogel et al. |
| 6,676,971 B2 | 1/2004 | Goupil et al. |
| 6,680,046 B1 * | 1/2004 | Boschetti ............ 424/9.1 |
| 6,710,126 B1 | 3/2004 | Hirt et al. |
| 6,790,456 B2 | 9/2004 | Vogel et al. |
| 6,911,219 B2 | 6/2005 | Matson et al. |
| 7,060,298 B2 | 6/2006 | Vogel et al. |
| 7,338,657 B2 | 3/2008 | Vogel |
| 7,442,385 B2 * | 10/2008 | Lewis et al. ............ 424/426 |
| 7,591,993 B2 | 9/2009 | Boschetti et al. |
| 7,670,592 B2 | 3/2010 | Boschetti |
| 2002/0068089 A1 | 6/2002 | Vogel et al. |
| 2002/0187172 A1 | 12/2002 | Reb et al. |
| 2003/0203976 A1 | 10/2003 | Hunter et al. |
| 2003/0203985 A1 | 10/2003 | Baldwin |
| 2003/0211083 A1 | 11/2003 | Vogel et al. |
| 2003/0211165 A1 | 11/2003 | Vogel et al. |
| 2003/0212022 A1 | 11/2003 | Vogel et al. |
| 2003/0215519 A1 | 11/2003 | Schwartz et al. |
| 2003/0233150 A1 | 12/2003 | Bourne et al. |
| 2004/0047804 A1 | 3/2004 | Wolf et al. |
| 2004/0091425 A1 | 5/2004 | Boschetti |
| 2004/0091543 A1 | 5/2004 | Bell et al. |
| 2004/0092883 A1 | 5/2004 | Casey et al. |
| 2004/0096514 A1 | 5/2004 | Vogel et al. |
| 2004/0101564 A1 | 5/2004 | Rioux et al. |
| 2004/0197302 A1 | 10/2004 | Porter et al. |
| 2005/0025708 A1 | 2/2005 | Vogel et al. |
| 2005/0158393 A1 | 7/2005 | Reb et al. |
| 2005/0265923 A1 * | 12/2005 | Toner et al. ............ 424/1.11 |
| 2006/0057198 A1 | 3/2006 | Lewis et al. |
| 2006/0063732 A1 | 3/2006 | Vogel |
| 2006/0251582 A1 | 11/2006 | Reb |
| 2007/0275991 A1 | 11/2007 | Lewis et al. |
| 2007/0281028 A1 | 12/2007 | Lewis et al. |
| 2008/0033366 A1 | 2/2008 | Matson et al. |
| 2008/0039890 A1 | 2/2008 | Matson et al. |
| 2008/0118569 A1 | 5/2008 | Vogel et al. |
| 2008/0220077 A1 | 9/2008 | Vogel et al. |
| 2008/0305176 A1 | 12/2008 | Lewis et al. |
| 2009/0022804 A1 | 1/2009 | Lewis et al. |
| 2009/0117196 A1 | 5/2009 | Boschetti |
| 2009/0186094 A1 | 7/2009 | Vogel |
| 2009/0220627 A1 | 9/2009 | Hasegawa |
| 2010/0119572 A1 | 5/2010 | Boschetti |
| 2011/0033508 A1 | 2/2011 | Vogel |
| 2011/0182998 A1 | 7/2011 | Reb et al. |

FOREIGN PATENT DOCUMENTS

| | | |
|---|---|---|
| EP | 0264166 | 4/1988 |
| EP | 0291177 | 4/1988 |
| EP | 0407569 | 9/1991 |
| EP | 0648480 | 4/1995 |
| EP | 0764047 | 4/2000 |
| EP | 0993337 | 9/2001 |
| EP | 0797988 | 4/2004 |
| EP | 1592405 | 8/2004 |
| EP | 1267839 | 7/2007 |
| EP | 1128816 | 5/2008 |
| EP | 0448391 | 10/2008 |
| FR | 2378808 | 8/1978 |
| FR | 2784580 | 9/2005 |
| JP | 49108168 | 10/1974 |
| JP | 53050290 | 5/1978 |
| JP | 57128709 | 8/1982 |
| JP | 5000969 | 1/1993 |
| JP | 05051473 | 3/1993 |
| JP | 6056676 | 3/1994 |
| WO | WO89/07455 | 8/1989 |
| WO | WO92/21327 | 12/1992 |
| WO | WO96/11671 | 4/1996 |
| WO | WO97/07783 | 3/1997 |
| WO | WO98/04198 | 2/1998 |
| WO | WO98/16265 | 4/1998 |
| WO | WO99/11196 | 3/1999 |
| WO | WO99/12577 | 3/1999 |
| WO | WO99/31167 | 6/1999 |
| WO | WO99/34829 | 7/1999 |
| WO | WO99/44643 | 9/1999 |
| WO | WO0023054 | 4/2000 |
| WO | WO01/70289 | 9/2001 |
| WO | WO0168720 | 9/2001 |
| WO | WO0172281 | 10/2001 |
| WO | WO03/084582 | 10/2003 |
| WO | WO2004/071495 | 8/2004 |
| WO | WO2005/087193 | 9/2005 |
| WO | WO2006/046155 | 5/2006 |
| WO | WO2006/119968 | 11/2006 |
| WO | WO2008/041001 | 4/2008 |
| WO | WO2010/062678 | 6/2010 |

OTHER PUBLICATIONS

Murata et al., 'Arterial Embolization Using Super Absorbent Polymer Microspheres (SAP-Microspheres) for Arteriovenous Malformation with Intractable Skin Ulcer'. J. Alchi Med. Univ. Assoc. 30:203-207, 2002.

(56) References Cited

OTHER PUBLICATIONS

Kissel et al., 'Injectable Bipdegradable Microspheres for Vaccine Delivery.' In: Microparticulate Systems for the Delivery of Proteins and Vaccines (S. Cohen ed.), (Drugs and the Pharmaceutical Sciences, vol. 77), Marcel Dekker, New York, NY, 1996.
Boschetti, 'Polymer Microbeads'. In. Microspheres, Microencapsulation and Liposomes (Arshady, R. ed.) John Wiley and Sons (New York, NY) vol. 2, 171-189, 1999.
Boschetti, 'Polyacrylamide Derivatives to the Service of Bipseparations'. J. Bipchem. Biophys. Meth. 19: 21-36, 1989.
Laurent et al., 'Trisceryl Gelatin Micrispheres for Therapeutic Embolization, I: Development and In Virto Evaluation.' Amer. J. Neuro. Radiol. 17: 533-540, 1996.
Inoue et al., 'Experimental Studies of Segmental Hepatic Artery Embolization with a Super Absorbent Embolic Agent'. Nippon Acta Radiologica 50: 1439-1441, 1990.
Dass et al., 'Microsphere-Mediated Targeted Gene Therapy of solid Tumors'. Drug Delivery 6: 243-252, 1999.
U.S. Appl. No. 09/528,989, Not published. Abandoned Oct. 16, 2008.
Bachtsi et al., 'An Experimental Investigation of Enzyme Release from Poly(vinyl alcohol) Crosslinked Microspheres'. J Microencapsulation 12(1): 23-35, 1995.
Thanoo et al., 'Preparation and Properties of Barium Sulphate and Methyl Lothalamate-Loaded Poly(vinyl alcohol) Microspheres as Radiopaque Particulate Emboli'. J of Applied Biomaterials 2:68-72, 1991.
Hori et al., 'An Experimental Study of a New Embolic Material—Lipiodol Suspension of Water-Absorbent Particle'. Nippon Acta Radiologica 53(1): 50-56, 1993.
Hori et al., 'A New Embolic Material: Super Absorbent Polymer Microsphere and its Embolic Effects'. Japanese J Intervent Radiol 11: 375-381, 1996.
Hori et al., 'Embolotherapy of Large Hepatocellular Carcinoma Using a New, Permanent, Spherical Embolic Maaterial Without Anti-Neoplastic Agents'. Cardiovasc Intervent Radiol 24 (Suppl 1) S203, 2001.
Iwase et al., 'Laproscopically Assisted Splenectomy Following Preoperative Splenic Artery Embolization Using Contour Emboli for Myclofibrosis with Massive Splenomegaly'. Surgical Laproscopy, Endoscopy & Percutaneous Techniques 9(3): 197-202, 1999.
Iwase et al., 'Splenic Artery Embolozation Using Contour Emboli before Laparoscopic of Laparoscopically Assisted Splenectomy'. Surgical Laparoscopy, Endoscopy & Percutaneous Techniques 12(5): 331-336, 2002.
Jiaqi, 'A New Embolic Material: Super Absorbent Polymer (SAP) Microsphere and its Embolic Effects'. Nippon Acta Radiologica 56(1): 19-24, 1996.
Khankan et al., 'Embolic Effects of Superabsorbent Polymer Microspheres in Rabbit Renal Model: Comparison with Trisacryl Gleatin Microspheres and Polyvinyl Alcohol'. Radiat Med 22(6): 384-390, 2004.
Kimura et al., 'Transcatherterial Embolization of AVM in Pancreas'. Japanese J Clin Radiol 43: 311-314, 1998.
Kusano et al., 'Low-Dose Particulate Polyvinylalcohol Embolization in Massive Small Artery Intestinal Hemorrhage. Experimental and Clinical Results'. Invewtigative Radiology 22: 388-392, 1987.
Mavligit et al., 'Gastrointestinal Leimyosarcoma Metastatic to the Liver'. Cancer 75(8):2083-2088, 1995.
Muller-Schulte et al., 'Novel Magnetic Micrispheres on the Basis of Poly(vinyl alcohol) as Affinity Medium for Quantitative Detection of Glycated Haemoglobin'. J of Chromatography A 711: 53-60, 1995.
Osuga et al., 'Management of Advanced Pelvic Bone Tumors by Transarterial Embolotherapy Using SAP-Microspheres. A Preliminary Report'. Cardiovasc Intervent Radiol 22: S130, 1999.
Osuga et al., 'A New Embolic Material: SAP-Microsphere'. Japanese Journal of Clinical Medicine 59 Supp 6: 534-538, 2001.
Ogusa et al. 'Transarterial Embolization for Large Hepatocellular Carcinoma with use of Superabsorbent Poymer Microspheres: Initial Experience'. J Vasc Intervent Radiol 13(9 pt 1) 929-934, 2002.

Osuga et al., 'Embolization of High Flow Arteriovenous Malformations: Experience with Use of Superabsorbent Polymer Microspheres'. J Vasc Intervent Radiol 13(11): 1125-1133, 2002.
Tao et al., 'Study on Microspheres for Embolization of Hepatic Artery'. Acta Pharmaceutica Sinica 23(1): 55-60, 1988.
Wakhloo et al., 'Extended Preoperative Polyvinly Alcohol Microembolization of Intracranial Meningiomas: Assessment of Two Embolization Techniques'. American Journal of Neurology 14: 571-582, 1993.
Zou et al., 'Experimental Canine Hepatic Artery Embolilzation with Polyvinyl Alcohol Microsphere'. Zhonghua Fang She Zue Za Zhi 23(6): 330-332, 1989.
Hori et al., 'Vessel Embolic Materials'. Intervent Radiol 33: 109-112, 1999.
'A Study of Development and Practical Uses of New Arterial Embolic Materials (Super Waterabsorbent Resins)'. Innervision 13: 24, 1998.
Beltrami et al., 'Drug Loading conditions for Highly Dosed Crosslinked PVA Matrices with Controlled Release Properties'. Proc. Intl. Symp. Rel. Bioact. Mater. 15: 46-47, 1988.
Dion et al., 'Dextran Microsphere Embolization: Experimental and Clinical Experience with Radiologic-Pathologic Correlation'. Radiol. 160: 7174-721, 1986.
Flandroy et al., 'Clinical Applications of Microshoeres in Embolization and Chemoembolization: A Comprehensive Review and Perspectives'. In: Pharmaceitical Particulate Carriers in Medical Applications, vol. 61, pp. 321-366, 1993.
Thanoo et al., 'Barium Sulphate-Loaded p(HEMA) Microspheres as Artificial Emboli: Preparation and Properties'. Biomaterials 11: 477-481, 1990.
Thanoo et al., 'Radiopaque Hydrogel Microspheres'. J. Microencapsulation 6: 233-244, 1989.
Okada et al., 'A New Concept for Interpretation of First-Order Release from Albumin Microspheres'. J. Microencapsulation 8: 483-496, 1991.
Motohashi et al., 'Superabsorbent Sumikagel®'. 35-47, 1985 [English translation].
Laurent et al., 'Etude Histologique de Plusieurs Materiaux D'Embolization et D'Un Nouveau Type de Materiel Soherique et Adhesif'. Innov. Tech. Biol. Med. 10: 358-366, 1989 [French].
Korsmeyer et al., 'Effect of the Morphology of Hydrophilic Polymeric Matrices on the Diffusion and Release of Water Soluble Drugs'. J. Membr. Sci. 9: 211-227, 1981.
Hosaka et al., 'Controlled Release of Drugs from Hydrogel Matrices'. J. Appl. Polymer Sci. 23: 2089-2098, 1979.
Horak et al., 'Hydrogels in Endovascular Embolization. I. Spherical Particles of Poly(2-hydroxyethyl Methacrylate) and Their Medico-Biological Properties'. Biomaterials 7: 188-193, 1986.
Horak et al., 'Hydrogels in Endovascular Embolization. II. Clinical Use of Spherical Particles'. Biomaterials 7: 467-470, 1986.
Horak et al., 'Hydrogels in Endovascular Embolization. III. Radiopaque Spherical Particles, Their Preparation and Properties'. Biomaterials 8: 142-145, 1987.
Horak et al., 'Hydrogels in Endovascular Embolization. IV. Effect of Radiopaque Spherical Particles on the Living Tissue'. Biomaterials 9: 367-371, 1988.
Graham et al., 'Hydrogels for controlled Drug Delivery'. Biomaterials 5: 27-36, 1984.
Gander et al., 'Effects of the Method of Drug Incorporation and the Size of the Monolith on Drug Release from Cross-linked Polymers'. Intl. J. Pharmacrutics 58: 63-71, 1990.
Forni et al., 'Influence of Drug Loading Level on Drug Release and Dynamic Swelling of Crosslinked Gelatin Microspheres'. J. Microencapsulation 9: 29-39, 1992.
Horak et al. 'Targeted Chemoembolization of Tumors with Poly(2-Hydroxyethyl Methacrylate) Particles'. Journal of Biomedical Material Research vol. 51 PT2 p. 184-190, 2000.
Horak et al., 'Biologically Active Thrombin-Containing Hydrogels Based on Poly(2-Hydroxyethyl Methacrylate) for Endovascular Occlusion'. Polymers in Medicine vol. 21 p. 31-41, 1991.
Laurent, 'Materials and Biomaterials for Interventional Radioloby', Biomedicine and Pharmacology vol. 52 PT2 p. 76-88, 1998.

(56) References Cited

OTHER PUBLICATIONS

Mestiri et al. 'Preparation and Characterization of Cisplatin-Loaded Polymethyl Methacrylate Microspheres'. International Journal of Pharmaceutics vol. 89 PT3 p. 229-234, 1993.
Jayakrishnan et al., 'Endovascular Embolization Using Hyraoget Microspheres'. J. Mater. Sci. Med. vol. 5 PT9-10 p. 723-727, Sep. 1994.
El-Samaligy et al., 'Effect of Aqueous Phase Modifiers on Drug Release from Polyacrylamide Microbeads'. Polyacrylamide Microbeads, Pharm. Ind. 48 NR9 p. 1070-1074, 1986.
El-Samaligy et al., Polyacrylamide Microbeads, A Sustained Release Drug Delivery System. International Journal of Pharmaceutics 13 p. 23-34, 1983.
Hernigou et al., 'Methotrexate Diffusion from Acrylic Cement'. J. Bone Joint Surgery 71-B p. 804-811, 1989.
Lee et al., 'Doxorubicin-Loaded QuadraSphere Microspheres: Plasma Pharmacokivetics and Intratumoral Drug Concentration in an Animal Model of Liver Cancer'. Cardiovasc. Intervent. Radiol. 33:576-582, 2010.
Grosso et al., 'Intra-Arterial Chemoembolization of HCC with Embolizing Microspheres Hepasphere Loaded with Chemotherapeutic Agent'. Cardiovasc. Intervent. Radiol. 31: 1141-1149, Sep. 13-17, 2008.
Lewis et al., 'Pharmacokinetic and Safety Study of Doxorubicin-Eluting Beads in a Porcine Model of Hepatic Embolization'. J. Vasc. Interven. Radiol. 17: 335-342, 2006.
Horak et al., 'Hydrogels in Endovascular Embolization: V. Antitumour Agent Methotrexate-Containing p(HEMA)'. Biomaterials vol. 13 (6), 1992.
Gonzalez et al., 'Drug-Eluting Beads: A New Paraidigm for the Treatment of Primary Liver Cancer'. EJHPP vol. 12 p. 54-56, 2006.
Lewis et al., 'Doxorubicin Eluting Beads—1: Effects of Drug Loading on Bead Characteristics and Drug Distribution'. J. Matr. Sci. Mater. Med. 18: 1691-1699, 2007.
Lee et al., 'Powerpoint Presentation: Doxorubicin Loaded Poly(Vinyl Alcohol-Sodium Acrylate) Co-Polymer Microspheres: Hepatic Arterial Delivery into Vx-2 Liver Tumor Model in Rabbit'. Division of Vascular and Interventional Radiology, John Hopkins University School of Medicine, 2008.
Laurent, 'Microspheres and NonSpherical Particles for Embolization'. Elsevier Inc. p. 248-256, 2007.
Office Action dated Jul. 15, 2005 for U.S. Appl. No. 10/220,982.
Office Action dated Jan. 20, 2006 for U.S. Appl. No. 10/220,982.
Office Action dated Aug. 1, 2006 for U.S. Appl. No. 10/220,982.
Office Action dated Jun. 11, 2007 for U.S. Appl. No. 10/220,982.
Office Action dated Oct. 12, 2007 for U.S. Appl. No. 10/220,982.
Office Action dated Mar. 21, 2008 for U.S. Appl. No. 10/220,982.
Office Action dated Nov. 18, 2008 for U.S. Appl. No. 10/220,982.
Office Action dated Jan. 29, 2010 for U.S. Appl. No. 10/220,982.
Office Action dated Oct. 20, 2010 for U.S. Appl. No. 10/220,982.
Office Action dated Feb. 14, 2011 for U.S. Appl. No. 12/122,590.
Office Action dated Aug. 1, 2011 for U.S. Appl. No. 12/122,590.
Office Action dated Jan. 23, 2008 for U.S. Appl. No. 11/430,789.
Office Action dated Sep. 12, 2008 for U.S. Appl. No. 11/430,789.
Office Action dated Aug. 17, 2009 for U.S. Appl. No. 11/430,789.
Office Action dated Apr. 14, 2010 for U.S. Appl. No. 11/430,789.
Office Action dated Sep. 14, 2011 for U.S. Appl. No. 11/430,789.
Kim et al., 'Composite Poly (vinyl alcohol) Beads for Controlled Drug Delivery'. Pharmaceutical Research vol. 9 No. 1 p. 10-16, 1992.
Supplemental Reply dated Sep. 3, 2010 in opposition of counterpart EP Patent No. 1267839.
Information about the result of oral proceedings held Sep. 23, 2010 which was dated Sep. 27, 2010 for EP Patent No. 1267839.
Office Action dated Mar. 16, 2010 for U.S. Appl. No. 10/919,257.
Office Action dated Apr. 8, 2010 for U.S. Appl. No. 11/253,435.
Aliberti et al., 'Trans-Arterial Chemoembolization (TACE) of Liver Metastases from Colorectal Cancer Using Irinotecan-Eluting Beads: Preliminary Results'. Anticancer Res. 26(5B): 3793-5, Sep.-Oct. 2006.
Bala et al., 'PLGA Nanoparticles in Drug Delivery: The State of the Art'. Crit Rev Ther Drug Carrier Syst. 21(5): 387-422, 2004.
Ball et al., 'In vitro Stability of Tris-Acryl Gelatin Microspheres in a Multipharmaceutical Chemoembolization Solution'. J Vasc Interv Radiol 14(1): 83-8, Jan. 2003.
Barr et al., 'Polyvinyl Alcohol Foam Particle Sizes and Concentrations Injectable Through Microcatheters'. J Vasc Interv Radiol 9(1 Pt 1): 113-8, Jan.-Feb. 1998.
Bilbao et al., 'Comparative Study of Four Different Spherical Embolic Particles in an Animal Model: A Morphologic and Histologic Evaluation'. J Vasc Interv Radiol Nov. 2008, 19(11): 1625-38, Epub Sep. 26, 2008.
Borovac et al., 'Release of Ibuporfen from Beads for Embolization: In Vitro and In Vivo Studies'. J Control Release Oct. 27, 2006, 115(3): 266-74, Epub Aug. 17, 2006.
Chen et al., 'Evaluation of Ion-Exchange Microspheres as Carriers for the Anticancer Drug Doxorubicin: In-Vitro Studies'. J Pharm Pharmacol. 44(3): 211-5, Mar. 1992.
Dunn, 'The Peculiarities of Polyvinyl Alcohol'. Chemistry and Industry, Issue 20, p. 801-806, 1980.
Fiorentini, 'Intraarterial Hepatic Chemoembolizaion of Liver Metastases from Colorectal Cancer Adopting Irinotecan-Eluting Beads: Results of a Phase II Clinical Study'. In Vivo 21(6): 1085-91, Nov.-Dec. 2007.
Guo et al., 'Ion-Exchange Resins as Drug Delivery Carriers'. J Pharm Sci 98(11): 3886-902, Nov. 2009.
Hong et al., 'New Intra-Arterial Drug Delivery System for the Treatment of Liver Cancer: Preclinical Assessment in a Rabbit Model of Liver Cancer'. Clin Cancer Res 12(8): 2563-7, Apr. 15, 2006.
Jordan et al., 'Comparative Study of Chemoembolization Loadable Beads: In Vitro Drug Release and Physical Properties of DC Bead and Hepasphere Loaded with Doxorubicin and Irinotecan'. J Vasc Interv Radiol 21(7): 1084-90, Jul. 2010.
Kawauchi et al., 'TACE with Antrocyclin Loaded HepaShoere for Intractable Hepatocellular Carcinoma'. Poster presentation at Cardiovascular and Interventional Radiological Society of Europe, Copenhagen, Denmark, Sep. 13-17, 2008.
Kettenbach et al., 'Drug-Loaded Microspheres for the Treatment of Liver Cancer: Review of Current Results'. Cardiovasc Intervent Radiol May-Jun. 2008, 31(3): 468-76, Epub Jan. 29, 2008.
Lammer et al., 'Prospective Ramdomized Study of Doxorubicin-Eluting Bead Embolization in the Treatment of Hepatocellular Carcinoma: Results of Precision V Study'. Cardiovasc. Intervent. Radiol. Jun. 2010, 33(3): 576-82, Epub Nov. 12, 2009.
Lewis et al., 'Comparative in Vitro Evaluation of Microspherical Embolisation Agents'. J Mater Sci Mater Med 17(12): 1193-204, Dec. 2006.
Liu et al., 'A Study of Doxorubicin Loading onto and Release from Sulfopropyl Dextran Ion-Exchange Microspheres'. J Control Release 77(3): 213.24, Dec. 13, 2001.
Malagari et al., 'Transarterical Chemoembolization of Unresectable Hepatocellular Carcinoma with Drug Eluting Beads: Results of an Open-Label Study of 62 Patients'. Cardiovasc Intervent Radiol Mar.-Apr. 2008, 31(2): 269-80, Epub Nov. 13, 2007.
Motycka et al., 'Effect of Methotruxated sorbed on Modified 2-Hydroxyethylmethacrylate Carriers in Mice of C3H Strain with a Solid Gardner Lymphosarcoma'. Neoplasm 24(3): 271-6, 1977.
Novak, 'Embolization Materials'. In Interventional Radiology, Dondelinger, R.F. et al., eds., Thieme Medical Publishers, NY, pp. 295-313, 1990.
Okitsu et al., 'TACE for Breast Cancer Liver Metastases using HepaSphere'. Poster presentation at Cardiovascular and Interventional Radiological Society of Europe, Copenhagen, Denmark, Sep. 13-17, 2008.
Osuga et al., 'Bland Embolization of Hepatocellular Carcinoma using Superabsorbent Polymer Microspheres'. Cardiovasc Intervent Radiol, Nov.-Dec. 2008, 31(6): 1108-16, Epub Jun. 10, 2008.
Poggi et al., 'Transhepatic Arterial Chemoembolization with Oxaliplatin-Eluting Microspheres (OEM-TACE) for Unresectable Hepatic Tumors'. Anticancer Res 28(6B): 3835-42, Nov.-Dec. 2008.

(56) References Cited

OTHER PUBLICATIONS

Qian et al., 'Application of Poly-Lactide-Co-Glycolide-Microspheres in the Transarterial Chemoembolization in an Animal Model of Hepatocellular Carcinoma'. World J Gastroenterol 9(1): 94-8, Jan. 2003.
Rump, 'Pharmacokinetics of Intraarterial Mitloycin C in the Chemoembolization Treatment of Liver Metastases'. Cen Pharmacol 27(4): 669-71, Jun. 1996.
Sottani, 'Validation of an LC-MS/MS Method for the Determination of Epirubicin in Human Serum of Patients Undergoing Drug Eluting Microsphere-Transarterial Chemoembolization (DEM-TACE)'. J Chromatogr B Analyt Technol Biomed Life Sci 877:3543-8, Epub Sep. 19, 2009.
Stastny et al., 'HPMA-Hydrogels containing Cytostatic Drigs. Kinetics fo the Drug Release and In Vivo Efficacy'. J control Release 81(1-2): 101-11, May 17, 2002.
Tang et al., 'Preservation of the Active Lactone form of Irinotecan using Drug Eluting Beads for the Treatment of Colorectal Cancer Metastases'. J Control Release 127: 70-8, Epub Dec. 23, 2007.
Tasdelen, 'Preparation, Characterization and Drug-Release Properties of Poly(N-Isopropylacrylamide) Microspheres Having Poly(Itaconic Acid) Graft Chains'. J Appl Polymer Sci 97:1115-1124, 2005. Taylor et al., 'Irinotecan Drug eluting Bease for use in chemoembolization: In vitro and In Vivo Evaluation of Drug Release Properties'. Eur J Pharm Sci Jan. 2007, 30(1): 7-14, Epub Sep. 15, 2006.
Tomashefski et al., 'Longterm Histopathologic Follow-up of Bronchial Arteries after Therapeuic Embolization with Polyvinyl Alcohol (Ivalon) in Patients with Cystic Fibrosis'. Hum Pathol 19(5): 555-61, May 1988.
Vallee et al., 'In Vitro Study of the Compatibility of Tris-Acryl Gelatin Microspheres with Various Chemotherapeutic Agents'. J Vasc Interv Radiol 14(5): 621-8, May 2003.
Varela et al., 'Chemoembolization of Hepatocellular Carcinoma with Drug Eluting Beads: Efficacy and Doxorubicin Pharmacokinetics'. J Hepatol. Mar. 2007, 46(3): 474-81, Epub Nov. 29, 2006.
Wassef, 'Anti-Inflammatory Effect of Ibuprofen-Loaded Embolization Beads in Sheep Uterus'. J Biomed Mater Res B Appl Biomater 86(1): 63-73, Jul. 2008.
Jones et al., 'Inhibition of Angiogenesis by Nonseroidal Anti-Inflammatory Drugs: Insight into Mechanisms and Implications for Cancer Growth and Ulcer Healing'. Not Med. 5(12): 1418-23, Dec. 1999.
Hatziapostolou et al., 'Different Inhibitors of Plasmin Differentially Affect Angiostatin Production and Angiogenesis'. Eur J Pharmacol 460(1): 1-8, Jan. 26, 2003.
Reply filed in Opposition of EP1267839 dated Aug. 23, 2010.
Reply filed in Opposition of EP1267839 dated Aug. 19, 2010.
Tsung et al., 'Preparation and Characterization of Glelatin Surface Modified PLGA Microspheres'. AAPS PharmSci. 3(2): E11, 2001.
Derdeyn et al., 'Polyvinyl alcohol Particle Size and Suspension Characteristics'. AJNR Am. J. Neuroradiol. 16(6): 1335-1343, 1995.
Falini et al., 'Polyvinyl Alcohol Particle Superficial Morphology'. AJNR Am J Neuroradiol 18(1): 194-195, 1997.
Gelfoam Product Insert, available at http://www.pfizer.com/pfizer/download/uspi_gelform_poweder.pdf 2005.
Herrmann et al., 'Uber den Poly-vinylalkohol'. Berichte 60: 1658-1663, 1927 English Abstract.
Laurent et al., 'Recanalization and Particle Exclusion after Embolization of Uterine Arteries in Sheet: A Long-Term Study'. Fertil.steril. 91(3): 884-892, 2009.
Leeds, 'Vinyl Polymers (Alcohol)'. In Encyclopedia of Chemical Technology, Kirkothmer ed., 21: 353-368, Wiley-Interscience, New York, 2nd ed., 1970.
McDowell et al., 'Some Relationships Between Polyvinyl Acetates and Polyvinyl Alcohols'. J Am Soc 62: 415, 1940.
Norrby et al., 'Angiogenesis: New Aspects Relating to its Intitation and Control'. APMIS 105: 417-437, 1997.
O'Reilly, 'The Preclinical Evaluation of Angiogenesis Inhibitors'. Investigational New Drugs 15: 5-13, 1997.
Pelage et al., 'Uterine Artery Embolization in Sheep: Comparison of Acute Effects with Polyvinyl Alcohol Particles and Calibrated Microspheres'. Radiology 224(2): 436-445, 2002.
Steward et al., 'Doxorubicin Plus Ifosfamide with rhGM-CSF in the Treatment of Advanced Adult Soft Tissue Sarcomas: Preliminary Results of a Phase II Study from the EORTC Soft-Tissue and Bone Sarcoma Group'. J. Can. Res. Clin. Oncol. 117(Suppl IV): S193-S197, 1991.
Office Action dated Aug. 4, 2009 for U.S. Appl. No. 10/919,257.
Office Action dated Jul. 23, 2009 for U.S. Appl. No. 12/348,867.
Notice of Allowability dated Dec. 7, 2009 for U.S. Appl. No. 12/348,867.
Office Action dated Sep. 14, 2009 for U.S. Appl. No. 11/253,435.
Summons to Oral Proceedings and Opposition Division Preliminary Opinion dated Jun. 30, 2009 for EP1267839.
Horak et al., 'Poly(2-Hydroxyethyl Methacrylate) Beads for the Preoperative Endovascular Occlusion of Branches of the Hepatic Artery in Focal Alterations of the Liver'. Clinical Materials 6: 287-297, 1990.
Staudinger et al., 'Uber die Konstitution von Hockpolymeren Kunststoffen'. Journal fur Praktische Chemie N.F. 155: 261-298, 1940.
Supplemental Letter in Notice of Opposition dated Oct. 1, 2008 for EP1267839.
Patentee Reply in Opposition dated Mar. 19, 2009 for EP1267839.
Office Action dated Nov. 30, 1995 for U.S. Appl. No. 08/150,148.
Office Action dated Jun. 3, 1996 for U.S. Appl. No. 08/150,148.
Notice of Allowability dated Sep. 20, 1996 for U.S. Appl. No. 08/150,148.
Office Action dated Oct. 16, 1995 for U.S. Appl. No. 08/471,303.
Office Action dated May 7, 1996 for U.S. Appl. No. 08/471,303.
Notice of Allowability dated Dec. 23, 1996 for U.S. Appl. No. 08/471,303.
Office Action dated Jul. 19, 2000 for U.S. Appl. No. 09/263,773.
Office Action dated Apr. 20, 2001 for U.S. Appl. No. 09/263,773.
Notice of Allowability dated Aug. 17, 2001 for U.S. Appl. No. 09/263,773.
Office Action dated Mar. 22, 2001 for U.S. Appl. No. 09/528,990.
Office Action dated Oct. 29, 2001 for U.S. Appl. No. 09/528,990.
Interview Summary dated Apr. 4, 2002 for U.S. Appl. No. 09/528,990.
Notice of Allowability dated Apr. 9, 2002 for U.S. Appl. No. 09/528,990.
Supplemental Notice of Allowability dated May 13, 2002 for U.S. Appl. No. 09/528,990.
Office Action dated Apr. 11, 2001 for U.S. Appl. No. 09/528,989.
Office Action dated Sep. 24, 2001 for U.S. Appl. No. 09/528,989.
Office Action dated Feb. 12, 2003 for U.S. Appl. No. 09/528,989.
Office Action dated Nov. 26, 2003 for U.S. Appl. No. 09/528,989.
Notice of Allowability dated Dec. 7, 2004 for U.S. Appl. No. 09/528,989.
Office Action dated Sep. 19, 2005 for U.S. Appl. No. 09/528,989.
Office Action dated Jan. 19, 2007 for U.S. Appl. No. 09/528,989.
Office Action dated Sep. 20, 2007 for U.S. Appl. No. 09/528,989.
Office Action dated Feb. 27, 2008 for U.S. Appl. No. 09/528,989.
Office Action dated Aug. 27, 2001 for U.S. Appl. No. 09/528,991.
Office Action dated May 21, 2002 for U.S. Appl. No. 09/528,991.
Notice of Allowability dated Jul. 2, 2003 for U.S. Appl. No. 09/528,991.
Office Action dated Aug. 24, 2005 for U.S. Appl. No. 10/220,984.
Office Action dated Apr. 18, 2006 for U.S. Appl. No. 10/220,984.
Office Action dated Jan. 10, 2007 for U.S. Appl. No. 10/220,984.
Notice of Allowability dated Oct. 18, 2007 for U.S. Appl. No. 10/220,984.
Office Action dated May 19, 2003 for U.S. Appl. No. 10/029,294.
Office Action dated Mar. 24, 2004 for U.S. Appl. No. 10/029,294.
Office Action dated Jan. 6, 2005 for U.S. Appl. No. 10/029,294.
Notice of Allowability dated Feb. 1, 2006 for U.S. Appl. No. 10/029,294.
Notice of Allowability dated May 6, 2004 for U.S. Appl. No. 10/222,819.
Office Action dated Mar. 19, 2007 for U.S. Appl. No. 10/704,919.
Office Action dated Jan. 9, 2008 for U.S. Appl. No. 10/704,919.

(56) References Cited

OTHER PUBLICATIONS

Office Action dated May 14, 2008 for U.S. Appl. No. 10/704,919.
Office Action dated Feb. 3, 2009 for U.S. Appl. No. 10/704,919.
Office Action dated Oct. 31, 2008 for U.S. Appl. No. 10/919,257.
Office Action dated Oct. 30, 2001 for U.S. Appl. No. 09/419,114.
Office Action dated Jul. 3, 2002 for U.S. Appl. No. 09/419,114.
Notice of Allowability dated Jul. 25, 2003 for U.S. Appl. No. 09/419,114.
Office Action dated Nov. 16, 2005 for U.S. Appl. No. 10/692,785.
Office Action dated Jun. 2, 2006 for U.S. Appl. No. 10/692,785.
Office Action dated Oct. 30, 2006 for U.S. Appl. No. 10/692,785.
Interview Summary dated Nov. 21, 2006 for U.S. Appl. No. 10/692,785.
Office Action dated Jul. 12, 2007 for U.S. Appl. No. 10/692,785.
Office Action dated Jan. 24, 2008 for U.S. Appl. No. 10/692,785.
Office Action dated Sep. 4, 2008 for U.S. Appl. No. 10/692,785.
Notice of Allowability dated Sep. 29, 2008 for U.S. Appl. No. 10/692,785.
Office Action dated Aug. 2, 2004 for U.S. Appl. No. 10/133,177.
Notice of Allowbility dated Feb. 18, 2005 for U.S. Appl. No. 10/133,177.
Office Action dated Mar. 18, 2004 for U.S. Appl. No. 10/220,983.
Office Action dated Sep. 9, 2004 for U.S. Appl. No. 10/220,983.
Office Action dated Mar. 9, 2005 for U.S. Appl. No. 10/220,983.
Office Action dated Apr. 6, 2007 for U.S. Appl. No. 11/253,435.
Office Action dated Feb. 26, 2008 for U.S. Appl. No. 11/253,435.
Office Action dated Nov. 18, 2008 for U.S. Appl. No. 11/253,435.
Office Action dated Jan. 29, 2003 for U.S. Appl. No. 09/945,793.
Office Action dated Jul. 21, 2003 for U.S. Appl. No. 09/945,793.
Office Action dated Apr. 29, 2004 for U.S. Appl. No. 09/945,793.
Interview Summary dated Dec. 22, 2004 for U.S. Appl. No. 09/945,793.
Office Action dated Nov. 18, 2005 for U.S. Appl. No. 11/030,182.
Interview Summary dated Jun. 29, 2006 for U.S. Appl. No. 11/030,182.
Cohen et al., 'Microparticulate Systems for the Delivery of Proteins and Vaccines'. Marcel Dekker (New York, NY) pp. 55, 56 & 59, 1996.
Lee et al., Presentation from the Society of Interventional Radiology (SIR) 33rd Annual Meeting held Mar. 15-20, 2008 in Washington, DC (Available at http://www.biospheremed.com/publication_files/JHH_SIR2008.pdf) Last visited Oct. 29, 2009.
Barnes et al., 'Fluorescence Imaging of Single Molecules in Polymer Microspheres'. Cytometry 36: 169-175, 1999.
Barton et al., 'Embolization of Bone Metastases'. J Vasc Interv Radiol 7: 81-88, 1996.
Beaujeux et al., 'Trisacryl Gelatin Microspheres for Therapeutic Embolization, II: Preliminary Clinical Evaluation in Tumors and Arteriovenous Malformations'. Am J Neuroradiol 17: 541-548, 1996.
Berge et al., 'Pharmaceutical Salts'. Jour Pharm Sci 66: 1-19, 1977.
Brown et al., 'Syntheses and Copolymerization s of New Water-Soluble Polyipdinated Acrylic Monomers'. Makromol Chem Rapit Commun 6: 503-507, 1985.
Dass et al., 'A Microsphere-Lipoplex (Microplex) Vector for Targeted Gene Therapy of Cancer. 1. Construction and In Vitro Evaluation'. Drug Delivery 6: 259-269, 2008.
de Luis et al., 'In Vivo Evaluation of a New Embolic Spherical Particle (HepaSphere™) in a Kidney Animal Model'. Cardiovasc Intervent Radiol 31: 367-376, 2008.
Eposito et al., 'Preparation and Characterization of Cationic Microspheres for Gene Delivery'. International Jour Pharm 189: 29-41, 1999.
Eppley et al., 'A Potential Biomaterial Composite for Dermal and Subcutaneous Augmentation'. Annals of Plastic Surgery 32(5): 463-468, 1994.
Finch, ed., 'Polyvinyl Alcohol, Properties and Applications'. pp. 1-640, Wiley, New York (Table of Contents only), 1973.
Horak et al., 'Haemostatic Activity of Ethamsylate and Aminocaproic Acid Absorbed Poly(2-Hydroxyethyl Methycrylate) Particles'. Biomaterials 13: 521-526, 1992.
Hori et al., 'Embolization Therapy of Arteriovenous Malformation of the Extremities'. IVR 11: 29-33, 1996.
Kalyanasundaram et al., 'Coacervate Microspheres as Crrriers of Reconbinant Adenoviruses'. Cancer Gene Therapy 6: 107-112, 1999.
Kitamura et al., 'Polymer with a High Water Absorption Property—Sumika Gel'. Sumitomo Chemical Special Issue 1-9, 1980.
Langer et al., 'Tissue Engineering'. Science 260: 920-926, 1993.
Marvel et al., 'The Structure of Vinyl Polymers. II. Polyvinyl Alcohol'. The Journal of the American Chemical Society 60: 1045, 1938.
Marvel et al., 'End Group Structures of Polyvinyl Alcohol'. The Journal of the American Chemical Society 65: 1710, 1943.
The Merck Index, 'Polysorbates'. 12th Ed., Merck & Col., Inc., p. 1308, 1996.
Notice of Opposition dated Jul. 1, 2008 for European Patent No. 1267839; and Grounds of Opposition, pp. 1-16.
Spongel®—Product Description Sheet, Yamanouchi Pharmaceutical, 1998.
Staudinger et al., 'Uber Poly-Vinylacetat und Poly-Vinylalkohol'. Berichte 60: 1782, 1927.
Chithambara et al., 'Preparation ad Properties of Barium Sulphate and Methyl Lothalamate Loaded Poly(vinyl alcohol) Microspheres as Radiopaque Particulate Emboli'. J of Applied Biomaterials 2: 68-72, 1991.
Iwase et al., 'Hand-Assisted Laparoscopic Spleenectomy for Idiopathic Thrombocytopenic Purpura During Pregnancy'. Surgical Laparoscopy, Endoscopy & Percutaneous Techniques 11(1): 53-56, 2001.
Beese et al., 'Renal Angiography Using Carbon Dioxide'. British Journal of Radiology 73: 3-6, 2000.
Benson, 'Highly Porous Polymers'. American Laboratory 35(10): 44, 2003.
Benson, 'Cavilink Drug Delivery Technology'. Available at http://www.polygenetics.com/patents.htm 2008.
Chawla, 'In vivo Magnetic Resonance Vascular Imaging Using Laser-Polarized 3He Microbubbles'. Proc Nat Acad Sci USA 95: 10832-10835, 1998.
Chawla, 'Hyperpolarized Gas as a Vascular Contrast Agent'. Center for In Vivo Microscopy located at http://www.civm.me.duke.edu/civmProjects/HPContrast.html, visited on Jul. 25, 2002.
Cherksey, 'Adrenal Chromaffin Cells on Microcarriers Exhibit Enhanced Long-Term Functional Effects When Implanted into the Mammalian Brian'. IBRO 657-664, 1996.
Finch, 'Properties and Applications'. Polyvinyl Alcohol, p. 640, Wiley, New York, 1973.
Grosso et al., 'Transarterial Chemoembolization for Hepatocellular Carcinoma with Drug-Eluting Microspheres: Preliminary Results from an Italian Multicentre Study'. Cardiovasc Intervent Radiol 31: 1141-1149, 2008. Epub ahead of print Aug. 12, 2008.
Hori et al., 'A Study of Development and Practical Uses of New Arterial Embolic Materials (Super Water-Absorbent Resins'. Innervision 13: 24, 1998.
Hori et al., 'Study on the Effect of Arterial Embolization with Super-Absorbent Polymer'. Intervent Radiol 11: 1-11, 1996.
Kim et al., 'Biodegradable Polymeric Microspheres with 'open/closed' Pores for Sustained Release of Human Growth Hormone'. Elsevier, Journal of controlled Release, vol. 112, pp. 167-174, 2006.
Kim et al., 'Gas Foamed Open Porous Biodegradable Polymeric Microspheres'. Elsevier Biomaterials, vol. 27, pp. 152-159, 2006.
Landgraf et al., 'New Polymer Enables Near Zero-Order Release of Drugs'. Drug Delivery Technology, 5(2): 48-55, 2005.
Landgraf et al., 'Polymer Microcarriers Exhibiting Zero-Order Release'. Drug Delivery Technology 3(1), 56-63, 2003.
Lewis et al., 'DC Bead: In Vitro Characterization of a Drug-Delivery Device for Transarterial Chemoembolization'. J Vasc Interv Radiol 17: 335-345, 2006.
Mandai et al., 'Direct Thrombosis of Aneurysms with Cellulose Acetate Polymer. Part I: Results of Thrombosis in Experimental Aneurysms'. J Neurosurgery 77: 497-500, 1992.
Marra et al., 'Bone Tissue Engineering'. CRC Press; Chapter 6, 'Biodegradable Polymers and Microspheres in Tissue Engineering'. pp. 1-27, 2005.

(56) References Cited

OTHER PUBLICATIONS

Osuga et al., 'Transarterial Embolization for Large Hepatocellular Carcimona with Use of Superabsorbent Polymer Microspheres: Initial Experience'. J Vasc Intervent Radiol 13(9 pt 1): 929-934, 2002.
Repa et al., 'Mortalities Associated with Use of a Commercial Suspension of Polyvinyl Alcohol'. Radiology 170(2): 395-399, 1989.
Schmedlen et al., 'Photocrosslinkable Polyvinyl Alcohol Hydrogels that can be Modified with Cell Adhesion Peptides for use in Tissue Engineering'. Elsevier, Biomaterials, vol. 23, pp. 4325-4332, 2002.
Schwarz et al., 'Transcatheter Embolization Using Degardable Crosslinked Hydrogels'. Elsevier, Biomaterials, vol. 25, pp. 5209-5215, 2004.
Sugawara et al., 'Experimental Investigations Concerning a New Liquid Embolization Method: Combined Administration of Ethanol-Estrogen and Polyvinyl Acetate'. Neuro Med Chir (Tokoyo) 33: 71-76, 1993.
Taki et al., 'A New Liquid Material for Embolization of Arteriovenous Malformations'. AJNR 11: 163-168, 1990.
Thanoo et al., 'Controlled Release of Oral Drugs from Cross-Linked Polyvinyl Alcohol Microspheres'. J Pharm Pharmacol 45: 16-20, 1993.
Vinters et al., 'The Histotoxicity of Cyanoacrylates: A Selective Review'. Neuroradioliogy 27: 279-291, 1985.
Ziegler et al. 'Angiogenesis Research Enjoys Growth Spurt in the 1990's'. Journal of the National Cancer Institute 88(12): 786-788, 1996.
Raoul et al., 'Chemoembolization of Hepatocellular Carcinomas'. Cancer 70 pp. 585-590, 1992.
Hexabrix®—Product description sheet, p. 1-4, 1996 (JP).
Imagenil®—Product description sheet, p. 1-4, 1997 (JP).
Office Action dated Aug. 23, 2005 for U.S. Appl. No. 10/029,294.
Brown et al., 'Synthese et Copolymerisation de Nouveaux Monomers Acryliques Diiodes et Triiodes'. Bulletin de la Societe Chimique de France 4: 669-677, 1986.
Thanoo et al., 'Tantalum Loaded Silicone Microspheres as Particulate Emboli'. J Microencapsulation, vol. 8 No. 1, p. 95-101, 1991.
Cavanagh et al., 'Prostatic Artery Embolization as a Primary Treatmen for Benign Prostatic Hyperplasia: Preliminary Results in Two Patients'. Cardiovascular Intervent Radiol, 2009.
Examiners Answer to Appeal Brief dated Dec. 20, 2011 for U.S. Appl. No. 10/220,982.
European Search Report dated Aug. 2, 2011 for EP07009639.1.
Office Action dated Mar. 29, 2012 for U.S. Appl. No. 13/371,964.
Peppas et al., 'Drug Diffusion and Binding in Ionizable Interpenetrating Networks from Poly(Vinyl Alcohol) and Poly(Acrylic Acid)', European Journal of Pharmaceitics and Bippharmaceutics vol. 46, pp. 15-29, 1998.
Notice of Allowance dated Mar. 30, 2012 for U.S. Appl. No. 11/430,789.
Office Action dated Aug. 13, 2009 for U.S. App. No. 10/220,982.
Reply Brief dated Feb. 21, 2012 for U.S. Appl. No. 10/220,982.
European Search Report dated Sep. 17, 2012 for EP11009832.4.
Office Action dated Nov. 26, 2012 for U.S. Appl. No. 13/371,964.

* cited by examiner

COMPOSITIONS AND METHODS USING MICROSPHERES AND NON-IONIC CONTRAST AGENTS

RELATED APPLICATIONS

This application is a continuation of co-pending U.S. patent application Ser. No. 11/430,789, filed May 9, 2006, titled "COMPOSITIONS AND METHODS USING MICROSPHERES AND NON-IONIC CONTRAST AGENTS," which claims the benefit of U.S. Provisional Application No. 60/679,348, filed May 9, 2005, each of which is incorporated herein by reference in its entirety.

FIELD OF INVENTION

The present invention relates to compositions and methods for treating diseases and disorders including cancer and various other angiogenic-dependent diseases, vascular malfunctions, arteriovenous malformations (AVM), hemorrhagic processes and treatment of pain, in particular tumor-related pain by drug delivery and/or therapeutic embolization using microspheres. More particularly the invention relates to microspheres containing non-ionic contrast agents, to compositions comprising these microspheres, as well as methods for preparing and using such compositions for drug delivery and/or embolization therapy. Furthermore, the invention relates to compositions and methods using detectable microspheres for targeted drug delivery, irrespective of whether embolization is also needed.

BACKGROUND OF INVENTION

Therapeutic vascular occlusions (embolizations) are techniques used to treat certain pathological conditions in situ and involve the injection of an embolic material into the vessel of concern. For example, blood vessels which nourish a tumor are deliberately blocked by injection of an embolic material into the vessel. Notably in the case of tumors, vascular occlusion can suppress pain, limit blood loss on the surgical intervention to follow embolization, or even bring on a tumoral necrosis and avoid the operation.

In the case of vascular malformations, such as AVM or arteriovenous fistulas, vascular occlusion enables the blood flow to the tissues to be normalized, aids in surgery, and limits the risk of hemorrhage. In hemorrhagic processes, vascular occlusion produces a reduction of flow, which promotes cicatrization of the arterial opening(s).

Embolization can be used in the treatment of uterine fibroids, postpartum and/post-caesarian bleeding, post-surgical vaginal bleeding, the prevention and/or treatment of hemorrhage from ectopic pregnancy, prophilatically prior to myomectomy and in obstetrical patients at high risk for bleeding, such as those patients with placenta previa, placenta accreta, and twin fetal death. Embolization can also be used to stop uncontrolled bleeding, or to slow bleeding prior or during surgery, and for sealing endoleaks into aneurysm sacs. Each of the above diseases or disorders is within the scope of the invention.

Furthermore, depending on the pathological conditions treated, drug delivery and/or therapeutic embolization can be carried out for temporary as well as permanent objectives.

Embolization is carried out generally by means of catheters making it possible to position particulate occlusion agents (emboli) in the circulatory system. For precise positioning some visual control is required. Therefore it is desired to use an embolic material that is suitably labeled by the addition of a contrast agent. For reducing the interference with the catheters, solid embolic materials are preferred over liquid embolic materials, which can stick to the catheter. Microspheres have been used as a suitable solid material in passive embolization, i.e., mechanical occlusion of particular vessels or sites in vivo.

A further advantage of microspheres is their potential as agents for drug delivery or for active embolization therapy. In drug delivery, the microspheres are used as a carrier for a drug/therapeutic or active agent, which is then released from the microspheres at the desired site in vivo, irrespective of whether mechanical blockage is desired or not. In active embolization therapy, the microspheres have a dual function: mechanical blockage (embolization) and highly localized, in situ delivery of a therapeutic agent. This agent can be used, for example, in the treatment of tumors with a chemotherapeutic or radiotherapeutic agent. This type of regional therapy can localize treatment at the site of the tumor. Potential site effects and damage to healthy tissue can thus be reduced, in particular when using cytotoxic chemotherapeutic or radiotherapeutic agents. Regional administration of the drug/agent (by active embolization or drug delivery) has the further advantage of increasing peak drug concentrations to the target tissue. This is not only advantageous for the administration of chemotherapeutic or radiotherapeutic agents but also for the administration of, for example, chemotherapeutic or pain relieving drugs.

However, the type of contrast agent loaded onto the microspheres has been found to alter the properties of the microspheres, such as reducing swellability of swellable materials, capacity to load additional components, such as a drug, or suitability to be injected by a catheter. Therefore, it is advantageous to provide microspheres suitable for embolization that are not only labeled but that are furthermore still capable of adsorbing or otherwise carrying a drug. Similarly, microspheres of the invention are useful for delivery of drugs or other therapeutics to particular cells, tissues or organs.

Thus, there is a demonstrated need for the further development of microspheres comprising a contrast agent, a drug, and/or another therapeutic agent which optionally can swell to sizes greater than their initial size. Therefore, it is an object of the present invention to provide contrast agent-containing microspheres with superior capacities for drug loading and/or delivery. It is another object of the invention to provide contrast agent-containing microspheres that have superior swelling properties. It is a further object of the invention to provide contrast agent-containing microspheres that have a hydrogel-like behavior. The contrast agent-containing microspheres can be suitable in active embolization therapy and/or in drug-delivery, and, in particular, for the treatment of angiogenesis-dependent diseases and/or relief of tumor-related pain.

SUMMARY OF INVENTION

In therapy, it is generally desirable to use microspheres that are visible to the practitioner during administration, and that the microspheres contain a drug which is slowly released at a low concentration so as to minimize the side-effects associated with the drug. Slow release is sufficient for the desired treatment since the microsphere is already at a location or target at which the drug is to be delivered. Additionally, the microsphere should have superior loading capacities, i.e., the microspheres are able to load a maximum amount of the drug in the presence of the contrast agent.

The most suitable microspheres for use in active embolization and/or drug delivery are based on hydrophilic polymers, such as hydrophilic polymers comprising hyodroxy and/or amine groups. In some embodiments, polymers or copolymers having positively charged groups or negatively charged groups or both can be used.

The microspheres may comprise a polymer or copolymer, such as, polyvinylalcohol (PVA), PVA-based polymers, PVA copolymers, or polymers or copolymers prepared from monomers based on acrylic acid, acryl amides, acrylates, i.e., acrylic acid esters and/or their derivatives, such as, for example, methacrylamide, methacrylate, methacrylic acid, etc. The polymers and/or copolymers may be cross-linked or not cross-linked.

In an embodiment in which acrylamides are used, the amino functionalities can be protonated to create positively charged groups. In embodiments in which acrylic acids are used, negatively charged groups can be created by deprotonating the acid functionality. In embodiments in which acrylic esters are used, ionic groups can be generated by hydrolyzing the ester groups. Ionic groups can also be generated by using suitable crosslinkers, in which case the resulting polymer or copolymer is cross-linked. The microspheres can also additionally have one or more or all of the properties described below.

In certain embodiments, the drug to be delivered is water soluble. In specific embodiments, the drug is in the form of a salt, such as a salt selected from the group consisting of hydrochloride, potassium chloride, ammoniumchloride, sodium sulphate or potassium sulphate. Additionally, the drug may have one or more or all the properties described in the detailed description of the invention.

It is an object of the invention to provide microspheres suitable for active embolization therapy and/or drug delivery comprising: (a) one or more hydrophilic or ionic polymer(s), and (b) a drug, such as a drug in the form of a salt, wherein the microsphere has the desired slow release properties of the drug and, in certain embodiments, superior drug loading capacity in the presence of a contrast agent and visibility to the practitioner when administering the microsphere to its target.

A suitable contrast agent for the above described system is a non-ionic contrast agent. The contrast agent may have one or more or all of the properties described in the detailed description of the invention.

In one embodiment, the invention provides compositions and methods for delivery of drugs, vaccines, polynucleotides, polypeptides, antibodies, polysaccharides, and/or diagnostic or imaging agents to a mammal, using microspheres as a carrier. In a most preferred embodiment, the invention provides microspheres comprising a non-ionic contrast agent for the delivery of at least one drug, a contrast agent, or a combination thereof.

In one embodiment, the invention provides a substantially spherical microsphere suitable for embolization and/or drug delivery, said microsphere comprising: (a) a biocompatible polymeric material comprising PVA, and (b) a non-ionic contrast agent; wherein the microsphere is swellable, for example, in a pharmaceutically acceptable solution and has a diameter of from about 10 µm to about 1000 µm before swelling. In some embodiments, the non-ionic contrast agent is selected from the group consisting of X-ray, computed tomography (CT), paramagnetic or superparamagnetic contrast agents, and, in a certain embodiment, the contrast agent contains iodine.

In another embodiment, the invention provides a substantially spherical microsphere suitable for embolization and/or drug delivery, said microsphere comprising: (a) a biocompatible polymeric material comprising PVA, (b) a non-ionic contrast agent, and/or (c) a drug, wherein the microsphere is swellable, for example, in a pharmaceutically acceptable solution and has a diameter of from about 10 µm to about 1000 µm before swelling. In some embodiments, the non-ionic contrast agent is selected from the group consisting of X-ray, CT, paramagnetic or superparamagnetic contrast agents, and, in a certain embodiment, the contrast agent contains iodine.

In a further embodiment, the invention provides a pharmaceutical composition comprising: (a) substantially spherical microspheres suitable for embolization and/or drug delivery, said microspheres comprising: (i) a biocompatible polymeric material comprising PVA, (ii) a non-ionic contrast agent, and (iii) a drug, wherein the microspheres are uniform in size and have a diameter of from about 10 µm to about 1000 µm; and (b) a pharmaceutically acceptable liquid. In some embodiments, the non-ionic contrast agent is selected from the group consisting of X-ray, CT, paramagnetic or superparamagnetic contrast agents, and, in a certain embodiment, the contrast agent contains iodine.

In another embodiment, the invention provides a pharmaceutical composition comprising: (a) substantially spherical microspheres suitable for embolization and/or drug delivery, said microspheres comprising: (i) a biocompatible polymeric material comprising PVA, (ii) a non-ionic contrast agent, and (iii) a drug, wherein the microspheres are uniform in size and have a diameter of from about 10 µm to about 1000 µm; and (b) a pharmaceutically acceptable liquid. In some embodiments, the non-ionic contrast agent is selected from the group consisting of X-ray, CT, paramagnetic or superparamagnetic contrast agents, and, in a certain embodiment, the contrast agent contains iodine.

In another embodiment, the invention provides substantially spherical microspheres suitable for embolization and/or drug delivery comprising: (a) non-crosslinked PVA, (b) a non-ionic contrast agent, and (c) a drug; wherein the microspheres are uniform in size and have a diameter of from about 10 µm to about 1000 µm. In certain embodiments, the drug is a chemotherapeutic or pain relieving drug.

In another embodiment, the invention provides substantially spherical microspheres suitable for embolization and/or drug delivery comprising: (a) non-crosslinked PVA, (b) a non-ionic X-ray contrast agent, and (c) a drug; wherein the microspheres are uniform in size and have a diameter of from about 10 µm to about 1000 µm.

In another embodiment, the invention provides substantially spherical microspheres suitable for embolization and/or drug delivery comprising: (a) non-crosslinked PVA, (b) a non-ionic contrast agent, and (c) a drug selected from the group consisting of doxorubicin, cisplatin, mitomycin C, tamoxifen, and paclitaxel; wherein the microspheres are uniform in size and have a diameter of from about 10 µm to about 1000 µm.

In another embodiment, the invention provides substantially spherical microspheres suitable for embolization and/or drug delivery comprising: (a) crosslinked PVA, (b) a non-ionic contrast agent, and (c) a drug selected from the group consisting of doxorubicin, cisplatin, mitomycin C, tamoxifen, and paclitaxel; wherein the microspheres are uniform in size and have a diameter of from about 10 µm to about 1000 µm.

In another embodiment, the invention provides substantially spherical microspheres suitable for embolization and/or drug delivery comprising: (a) crosslinked PVA, (b) a non-ionic X-ray contrast agent, and (c) a drug, wherein the microspheres are uniform in size and have a diameter of from about 10 µm to about 1000 µm.

In another embodiment, the invention provides substantially spherical microspheres suitable for embolization and/or drug delivery comprising: (a) crosslinked PVA, (b) a non-ionic contrast agent, and (c) a drug selected from the group consisting of doxorubicin, cisplatin, mitomycin C, tamoxifen, and paclitaxel; wherein the microspheres are uniform in size and have a diameter of from about 10 μm to about 1000 μm.

In another embodiment, the invention provides substantially spherical microspheres suitable for embolization and/or drug delivery comprising: (a) a polyvinylalcohol-acrylic acid copolymer, (b) a non-ionic contrast agent, and (c) a drug, such as a chemotherapeutic or pain relieving drug; wherein the microspheres are uniform in size and have a diameter of from about 10 μm to about 1000 μm. In some embodiments, the microspheres are swellable, for example, in a pharmaceutically acceptable solution. In certain embodiments, the polymer is a high water absorbing polymer. In specific embodiments, the polyvinylalcohol-acrylic acid copolymer is a vinyl alcohol and acrylate copolymer, such as a sodium acrylate polymer.

In another embodiment, the invention provides substantially spherical microspheres suitable for embolization and/or drug delivery comprising: (a) a polyvinylalcohol-acrylic acid copolymer, (b) a non-ionic X-ray contrast agent, and (c) a drug; wherein the microspheres are uniform in size and have a diameter of from about 10 μm to about 1000 μm. In some embodiments, the microspheres are swellable, for example, in a pharmaceutically acceptable solution. In certain embodiments, the polymer is a high water absorbing polymer. In specific embodiments, the polyvinylalcohol-acrylic acid copolymer is a vinyl alcohol and acrylate copolymer, such as a sodium acrylate polymer.

In another embodiment, the invention provides substantially spherical microspheres suitable for embolization and/or drug delivery comprising: (a) a polyvinylalcohol-acrylic acid copolymer, (b) a non-ionic contrast agent, and (c) a drug selected from the group consisting of doxorubicin, cisplatin, mitomycin C, tamoxifen, and paclitaxel; wherein the microspheres are uniform in size and have a diameter of from about 10 μm to about 1000 μm. In some embodiments, the microspheres are swellable, for example, in a pharmaceutically acceptable solution. In certain embodiments, the polymer is a high water absorbing polymer. In specific embodiments, the polyvinylalcohol-acrylic acid copolymer is a vinyl alcohol and acrylate copolymer, such as a sodium acrylate polymer.

In another embodiment, the invention provides substantially spherical microspheres comprising: (a) a polyvinylalcohol-acrylic acid copolymer, (b) a non-ionic contrast agent selected from the group consisting of iopamidol (Isovue™), iodixanol (Visipaque™), iohexol (Omnipaque™), iopromide (Ultravist™) and ioversol (Optiray™) and (c) a drug, such as a chemotherapeutic drug; preferably the drug is selected from the group consisting of doxorubicin, cisplatin, mitomycin C, tamoxifen, and paclitaxel; wherein the microspheres are uniform in size and have a diameter of from about 10 μm to about 1000 μm. In some embodiments, the microspheres are swellable, for example, in a pharmaceutically acceptable solution. In certain embodiments, the polymer is a high water absorbing polymer. In specific embodiments, the polyvinylalcohol-acrylic acid copolymer is a vinyl alcohol and acrylate copolymer, such as a sodium acrylate polymer.

In a further embodiment the invention provides an injectable pharmaceutical composition comprising the above microspheres and a pharmaceutically acceptable liquid.

In a further embodiment, the invention also provides a method for preparing a pharmaceutical composition comprising: (a) substantially spherical microspheres suitable for active embolization and/or drug-delivery, said microspheres comprising (i) a biocompatible polymeric material comprising PVA, (ii) a non-ionic contrast agent, wherein the microspheres are uniform in size and have a diameter of from about 10 μm to about 1000 μm; and (b) and a pharmaceutically acceptable liquid. The method comprises contacting the microspheres having a diameter ranging from about 10 μm to about 1000 μm with a solution containing a non-ionic contrast agent in a pharmaceutically acceptable liquid. In certain embodiments, the microspheres are swellable, for example, in the pharmaceutically acceptable solution, and have a diameter of 10 μm to 1000 μm before swelling. The microspheres may be optionally sterilized, for example, by irradiation (e.g., gamma- or beta irradiation).

In another embodiment, the invention provides a method of preparing the pharmaceutical composition comprising: (a) substantially spherical microspheres suitable for active embolization and/or drug delivery, said microspheres comprising (i) a biocompatible polymeric material comprising PVA, (ii) a non-ionic contrast agent, and (iii) a drug; wherein the microspheres are swellable, for example, in a pharmaceutically acceptable solution, are uniform in size, and have a diameter of from about 10 μm to about 1000 μm; and (b) a pharmaceutically acceptable liquid. The method comprises: (a) contacting the microspheres having a diameter ranging from about 10 μm to about 1000 μm with a solution of a non-ionic contrast agent in a pharmaceutically acceptable liquid in an amount of from about 10% to about 90% of what would be necessary to saturate the microspheres, and (b) adding a solution of a drug in a pharmaceutically acceptable solution until the microspheres are saturated. The microspheres may be optionally sterilized, for example, by irradiation (e.g., gamma- or beta irradiation).

In another embodiment, the invention provides a method of preparing an injectable pharmaceutical compositions comprising microspheres, said method comprising: (a) contacting swellable microspheres having a diameter ranging from 10 μm to 1000 μm, which comprise a biocompatible polymeric material comprising polyvinylalcohol, with a solution of a drug in an amount of from about 10% to about 90% of what would be necessary to saturate the microspheres, and (b) adding a solution of a non-ionic contrast agent in a pharmaceutically acceptable liquid until the microspheres are saturated. The microspheres may then be optionally sterilized, for example, by irradiation (e.g., gamma- or beta irradiation).

Within another embodiment, a method is provided for active embolization in a mammal which comprises administering to a mammal a microsphere according to the invention or a pharmaceutical composition according to the invention.

Within another embodiment, a method is provided for active embolization in a mammal which comprises administering to a mammal having an angiogenesis-dependent disease a microsphere according to the invention or a pharmaceutical composition according to the invention.

Within another embodiment, a method is provided for drug delivery in a mammal, with or without embolization, which comprises administering to a mammal a microsphere according to the invention or a pharmaceutical composition according to the invention.

Within another embodiment, a method is provided for drug delivery in a mammal, with or without embolization, which comprises administering to a mammal having an angiogenesis-dependent disease a microsphere according to the invention or a pharmaceutical composition according to the invention.

Within another embodiment, a method is provided for drug delivery in a mammal, with or without embolization, which comprises administering to a mammal having a tumor or other form of cancer a microsphere according to the invention or a pharmaceutical composition according to the invention. In certain embodiments, the microsphere or pharmaceutical composition is administered locally at the site of the tumor or other form of cancer, for example, directly into a tumor mass.

In other embodiments, a method is provided for the treatment of a tumor or other cancer in a mammal, which comprises administering to a mammal having the tumor or other form of cancer a microsphere according to the invention or a pharmaceutical composition according to the invention. In certain embodiments, the microsphere or pharmaceutical composition is administered locally at, or directly into, the site of the tumor or other form of cancer. In some embodiments, the tumor or other form of cancer is treated by localized drug delivery. In other embodiments, the tumor or other form of cancer is treated by localized drug delivery in combination with embolization.

Within another aspect of the present invention, methods are provided for treating tumor excision sites, comprising administering microspheres according to the invention or a pharmaceutical composition according to the invention to the resection margins of a tumor subsequent to excision, such that the local recurrence of cancer and the formation of new blood vessels at the site is inhibited.

Within other aspects, methods are provided for embolizing blood vessels in nontumorigenic, angiogenesis-dependent diseases, comprising delivering to the vessel microspheres or a pharmaceutical composition according to the invention, such that the blood vessel is effectively occluded.

Within other aspects, methods are provided for treating neovascular diseases of an organ comprising administering to a patient in need thereof microspheres according to the invention or a pharmaceutical composition according to the invention such that the formation of new blood vessels is inhibited.

Within other aspects, methods are provided for treating pain related to tumors comprising administering to a patient in need thereof microspheres according to the invention or a pharmaceutical composition according to the invention. In some embodiments the pain is treated by delivery of drug using a microsphere of the invention, either alone or in combination with embolization.

These and other aspects of the present invention will become evident upon reference to the following detailed description and attached drawings. In addition, various references are set forth below which are incorporated herein by reference in their entirety.

DETAILED DESCRIPTION OF THE INVENTION

For clarity of disclosure, and not by way of limitation, the detailed description of the present invention is divided into the subsections which follow.

Definitions

As used herein, "microspheres" means polymer or combinations of polymers made into bodies of various sizes. The microspheres can be in any shape, although they are often in substantially spherical shape. In certain embodiments, the microspheres are sterile, either alone or when in the form of an injectable solution. The microspheres may be sterilized by any method known in the art, for example, by irradiation, such as gamma- or beta irradiation. In some embodiments, the surface of the microsphere appears smooth under less than 1000-fold magnification. The microspheres of the present invention may comprise other materials as described and defined herein.

As used herein, "substantially spherical" generally means a shape that is close to a perfect sphere, which is defined as a volume that presents the lowest external surface area. Specifically, "substantially spherical" in the present invention means, when viewing any cross-section of the microsphere, the difference between the major diameter and the minor diameter is less than 20%, less than 10% or less than 5% depending on the embodiment used.

As used herein, the term "about" or "approximately" means within 20%, preferably within 10%, and more preferably within 5% (or 1% or less) of a given value or range.

As used herein, "cell adhesion promoter" in the present invention means any material that, because of their presence in or association with the microspheres, promotes or enhances the adhesiveness of cells to the surface of the microspheres. These materials are often proteins that are associated with the surface of the microspheres through covalent bonds or in an interpenetrated polymeric manner.

As used herein, "therapeutic agent" in the present invention refers to any substance that provides therapeutic effects to the process of angiogenesis-dependent diseases or biological or physiological responses to the angiogenesis-dependent diseases. An example of a therapeutic agent is an anti-inflammation agent that prevents or reduces the effect of inflammations associated with angiogenesis-dependent diseases.

As used herein, "hydrophilic interaction" refers to molecules or portions of molecules which may substantially bind with, absorb and/or dissolve in water. This may result in swelling and/or the formation of reversible gels.

As used herein, "hydrophobic interaction" refers to molecules or portions of molecules which do not substantially bind with, absorb and/or dissolve in water.

As used herein, "swellable" microspheres refers to microspheres that are capable of being enlarged in size, yet retain substantially the same shape, upon certain conditions, such as contacting aqueous liquids or physiological fluids. In certain embodiments, the swellable microspheres can be enlarged to about 15 times of their original size or to about 64 times their original volume. In certain embodiments, swellable microspheres are enlarged to about 4 times their original size or 64 times in volume upon contact with saline (0.9% sodium chloride solution). In some embodiments "swellable" microspheres refers to microspheres that have the ability to absorb water. For example, in certain embodiments, the water absorption rate of a swellable microsphere is at least about 750 g/g. The degree of swelling can be controlled by controlling factors such as, for example, the solvents in which they are suspended, and specific polymers used to make the microspheres. In certain embodiments, the degree of crosslinking is adjusted, and in other embodiments, cross-linking is not adjusted or is not present. This property enables the microspheres to be injected through needles of, for example, 18 to 30 gauge or smaller, yet be enlarged and secured at the injection site and of sufficient size to avoid or reduce the chance of being eliminated by the lymphatic or immune system of the mammal.

As used herein, "high water absorbing polymers" refers to polymers that can absorb at least 5% of water by weight or that are capable of increasing their dry weight to about 20 times their original weight when absorbing water. In some embodiments, the microspheres are "superabsorbant polymers" that can up to about 300 times, up to about 400 times, up to about 500 times, up to about 600 times, up to about 700 times, or up to about 750 times or more of their initial weight of a physiological fluid. For example, 1 g of dry microspheres can absorb up to about 300 g, up to about 400 g, up to about 500 g, up to about 600 g, up to about 700 g, or up to about 750 g or more of deionized water at room temperature (25° C.) and under atmospheric pressure.

Microspheres of the present invention, in certain embodiments, can comprise particles that are "hydrophilic." As used herein, the term "hydrophilic" means that the particles can dissolve in, absorb, or mix easily with water or aqueous solutions.

A used herein, "injectable" means capable of being administered, delivered or carried into the body via syringe, catheters, needles or other means for injecting or infusing the microspheres in a liquid medium.

As used herein, "treat," "treatment" and "treating" refer to the reduction or amelioration of the progression, severity, and/or duration of a given disease resulting from the administration of one or more therapies (including, but not limited to, the administration of microspheres of the invention). In certain embodiments, the terms refer to the reduction of pain associated with one or more diseases or conditions.

As used herein, "administer" or "administration" refers to the act of injecting or otherwise physically delivering a substance as it exists outside the body (e.g., an antibody of the invention) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or symptoms thereof, are being treated, administration of the therapy (such as the microspheres of the invention) typically occurs after the onset of the disease or symptoms thereof. When a disease, or symptoms thereof, are being prevented, administration of the therapy (such as the microspheres of the invention) typically occurs before the onset of the disease or symptoms thereof.

The term "effective amount" as used herein refers to the amount of a therapy (e.g., a microsphere or composition of the invention) which is sufficient to reduce and/or ameliorate the severity and/or duration of a given disease and/or a symptom related thereto.

The term "host" as used herein refers to an animal, preferably a mammal, and most preferably a human.

The term "infant" as used herein refers to a human less than 24 months, preferably less than 16 months, less than 12 months, less than 6 months, less than 3 months, less than 2 months, or less than 1 month of age.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a given disease. Any additional therapy can be administered in any order with the other additional therapies. In certain embodiments, the microspheres of the invention can be administered in combination with one or more therapies (e.g., therapies that are not microspheres of the invention that are currently administered to prevent, treat, manage, and/or ameliorate a given disease or other symptom related thereto). Non-limiting examples of therapies that can be administered in combination with microspheres of the invention include analgesic agents, anesthetic agents, antibiotics, or immunomodulatory agents or any other agent listed in the *U.S. Pharmacopoeia and/or Physician's Desk Reference*.

As used herein, the terms "manage," "managing," and "management" refer to the beneficial effects that a subject derives from a therapy (e.g., microspheres of the invention), which does not result in a cure of the infection. In certain embodiments, a subject is administered one or more therapies to "manage" a given disease or one or more symptoms related thereto, so as to prevent the progression or worsening of the disease.

The term "pharmaceutically acceptable" as used herein means being approved by a regulatory agency of the Federal or a state government, or listed in the U.S. Pharmacopeia, European Pharmacopeia or other generally recognized pharmacopeia for use in animals, and more particularly in humans.

As used herein, the terms "prevent," "preventing," and "prevention" refer to the total or partial inhibition of a given disease; the total or partial inhibition of the development or onset of disease progression of given disease, or a symptom related thereto in a subject; the total or partial inhibition of the progression of a given disease or a symptom related thereto.

As used herein, the terms "subject" and "patient" are used interchangeably. As used herein, a subject is preferably a mammal such as a non-primate (e.g., cows, pigs, horses, cats, dogs, rats, etc.) and a primate (e.g., monkey and human), most preferably a human. In some embodiments, the subject is an infant, child, adult or elderly subject.

As used herein, the term "therapy" refers to any protocol, method and/or agent that can be used in the management, treatment and/or amelioration of a given disease, or a symptom related thereto. In certain embodiments, the terms "therapies" and "therapy" refer to a biological therapy, supportive therapy, and/or other therapies known to one of skill in the art, such as medical personnel, useful in the management or treatment of a given disease, or symptom related thereto.

Microspheres

In certain embodiments, the microspheres of the present invention are fluoroscopically visible. That is, in some embodiments, the microspheres are loaded with, associated with, or otherwise contain a suitable contrast agent, such as a non-ionic contrast agent. In some embodiments, the microspheres of the invention are fluoroscopically visible and comprise a drug. One such embodiment is a substantially spherical PVA-containing swellable microsphere comprising a non-ionic contrast agent, and an anti-cancer drug. Another embodiment is a substantially spherical PVA-containing swellable microsphere comprising a non-ionic contrast agent, and a chemotherapeutic or pain relieving drug.

In certain embodiments, the microspheres for use in the present invention are biocompatible, hydrophilic, substantially spherical, and non-toxic and comprise at least one polymer. In some embodiments, the polymer is a hydrophilic polymer. In specific embodiments, the polymer is a high water absorbing or superabsorbant polymer. In some embodiments, the microspheres, in its dry form, is swellable upon contact or other exposure to liquids, such as water, saline solution, buffer, or physiological fluids.

In certain embodiments, the microspheres are injectable through a needle of 18 gauge or smaller and are not capable of being eliminated by the immune or lymphatic system. In some embodiments, the polymers are coated with agents which promote cell adhesion. In specific embodiments, living cells are attached to the microspheres forming layers of cells therein or thereon that link with surrounding tissues and can enhance the long-term stability of the beads.

The microspheres are stable in suspension, which allows the microspheres to be formulated and stored in suspension and injected with different liquids. More specifically, the hydrophilic nature of the microspheres permits placing them in suspension, and in particular, in the form of sterile and pyrogenic (pyrogen-free) injectable solutions, while avoiding the formation of aggregates or adhesion to the walls of storage containers and implantation devices, such as catheters, syringes, needles, and the like.

Microspheres of the invention can be implanted, such as by injection, in various locations of the body. The polymeric material for use in the present invention is non-toxic to tissues and cells and is biocompatible, i.e. generally does not cause inflammation. The microspheres can maintain their general shape and position once implanted at a desired site. The microspheres of the present invention are compressible and, in specific embodiments, can be injected through needles of 18 gauge or smaller.

These properties can be achieved through two steps. First, the size of the microspheres before injection can be carefully controlled by using appropriate solvents, salt concentration and pH level, and determining the final size of the microsphere upon saturation. With the final size and the amount of liquid necessary to achieve saturation having been determined, the microspheres before injection can be adjusted to either remain in their original size or swell to a certain degree upon contact with the solvent. The swelling depends on the solvent used, including pH and ionic strength of the solvent. The pre-injection swelling is controlled so that the microspheres are easily injectable through 18 gauge or smaller needles (e.g., 30 gauge). Second, after injection and upon contacting with tissues at the injection site, the microspheres can further swell into predetermined size or retain their pre-injection size, either of which size will allow the microspheres to be secured at the site of injection. In certain embodiments, the microspheres also achieve an embolization effect. The degree of pre-injection swelling, and thus the after injection swelling, can be determined by the particular microspheres used and the nature and location of the deficiencies being treated and the solvent used for swelling.

The microspheres for use in the present invention are flexible, such that they can easily pass into and through injection devices and small catheters without being permanently altered, but the microspheres are also resistant to the muscle contraction stress generated during and after the implantation process. The microspheres are also thermally stable which allows for easy, convenient sterilization, and room temperature, refrigerated or frozen storage.

In certain embodiments, the microspheres are substantially spherical, i.e., they have a shape that is close to a perfect sphere, which is defined as a volume that presents the lowest external surface area. In some embodiments, the surface of the microsphere appears smooth under less than 1000-fold magnification.

The microspheres are swellable in a pharmaceutically acceptable liquid, such as water, buffer solutions, saline, body liquids, aqueous salt solutions. In some embodiments, the dry microspheres can swell to about 2 times, about 5 times, or about 10 times of the dry microsphere diameter when saturated with a liquid, such as deionized water at room temperature (25° C.).

In certain embodiments, the dry microspheres are high water absorbing polymers and/or superabsorbant polymers. As used herein, "superabsorbant" means that 1 g dry microsphere can absorb up to about 300 g, up to about 500 g, or up to about 700 g of deionized water at room temperature (25° C.) and under atmospheric pressure.

In certain embodiments, the microspheres are uniform in size. This means that the difference in diameter between individual microspheres is from about 0 μm to about 100 μm, from about 0 μm to about 50 μm, or from about 0 μm to about 25 μm. In some embodiments, the microspheres have differences in diameter of 100 μm or less, about 50 μm or less, about 25 μm or less, about 10 μm or less or about 5 μm or less.

An individual microsphere according to the invention can have a diameter ranging from about 10 μm to about 1000 μm, from about 10 μm to about 400 μm, from about 50 μm to about 100 μm, from about 100 μm to about 150 μm, from about 150 μm to about 200 μm, or from about 100 μm to about 400 μm in its dry form, i.e. before swelling. As used herein, "dry" microspheres are microspheres that have less than about 10%, less than about 7%, less than about 5% (such as about 4%-5%), less than about 3% or less than about 1% of a liquid, such as water. Dry microspheres can be in the form of a powder. In some embodiments, the diameter of the microsphere before swelling is from about 40 μm to about 1000 μm, about 40 μm to about 400 μm, about 50 μm to about 300 μm, about 50 μm to about 200 μm, about 70 μm to about 120 μm, about 10 μm to about 400 μm, about 10 μm to about 200 μm, about 10 μm to about 120 μm, about 10 μm to about 50 μm, about 53 μm to about 106 μm, about 106 μm to about 150 μm, about 150 μm to about 212 μm, about 200 μm to about 250 μm, about 212 μm to about 250 μm, about 250 μm to about 300 μm, about 300 μm to about 350 μm, about 350 μm to about 400 μm, about 400 μm to about 450 μm, or about 450 μm to about 500 μm.

Most preferably, the microspheres are in a population wherein greater than 68% have a diameter of ±20% of the mean, ±10% of the mean, or ±5% of the mean diameter. In one embodiment, the microspheres are in a population wherein greater than 75% have a diameter of ±20% of the mean, ±10% of the mean or ±5% of the mean diameter. For example, in one embodiment the microspheres have a diameter between about 200 μm to about 250 μm or about 212 μm to about 250 μm. In certain embodiments, the microspheres have a mean diameter of 225 μm, and, in some embodiments, 75% of the population has a range of ±10% of the 225 μm mean diameter (i.e., 225 μm±22.5 μm).

In specific embodiments, the dry microspheres swell when contacted with a pharmaceutically acceptable liquid. In their swollen or partially swollen form (i.e. when the microspheres are no longer a dry powder but are instead in the form of a suspension or a hydrogel), the microspheres can have a diameter ranging from about 40 μm to about 2000 μm, about 200 μm to about 2000 μm, about 500 μm to about 1500 μm, or about 1000 μm to about 1500 μm. The diameter of the microspheres can be determined, for example, microscopically. The diameter of the microspheres can also be determined by any one of a number of methods known to those skilled in the art, such as laser systems. In some embodiments, the dry microspheres swell to about 2 times, about 3 times, about 4 times, about 5 times, or about 6 times the diameter of the dry microsphere prior to swelling. Thus, in some embodiments, the diameter of the swollen microspheres may be from about 2 times to about 6 times the diameter of any of the dry microsphere diameters, or ranges of diameters thereof, disclosed elsewhere herein.

It is an aspect of the invention to provide microspheres containing (a) a polymeric material, (b) a non-ionic contrast agent, and (c) a drug, such as a drug in the form of a salt. In certain embodiments, the polymeric material comprises a polymer or copolymer selected from the group consisting of polyvinylalcohol, polyacrylamide, or polyacrylate. Preferably, the polymeric material further comprises charged groups, such as positively charged or negatively charged groups, which may be present, for example, as functional groups of a copolymer or a crosslinking unit or may be introduced by chemical modification of the polymers. The ionic group(s) may be positively charged group(s), negatively charged group(s) or both. In certain embodiments, the ionic group can be a protonated amino group or a deprotonated carboxylic acid group (e.g., hydrolyzed ester groups).

The polymeric material of the present invention includes, but is not limited to, an acrylic polymer or copolymer, a polyacrylamide polymer or copolymer, or a polyvinyacetate polymer or copolymer. The polymeric material can also contain a polylactic acid polymer or copolymer, a polyanhydride polymer or copolymer, a polyacrylonitrile polymer or copolymer, a polysaccharide polymer or copolymer, and mixtures thereof.

In some embodiments, the polymeric material comprises PVA. More preferably, the polymeric material comprises a PVA copolymer. The polymeric material may also comprise a polyacrylate polymer or copolymer. In certain embodiments, the polymeric material is a PVA-polyacrylate copolymer. In other embodiments, the polymeric material is a PVA-sodium acrylate copolymer.

Another suitable polymer is an acrylic acid polymer or copolymer. Yet another suitable material is an acrylamide polymer or copolymer.

The polymeric material may include one or more polymer(s), one or more polymer mixture(s), a copolymer, copolymer mixtures, or polymer-copolymer mixtures.

In certain embodiments, the polymeric material is substantially hydrophilic. This means the microspheres contain at least one hydrophilic polymer or copolymer but it may also include the presence of hydrophobic polymers or copolymers as long as the overall characteristic of the microsphere are substantially hydrophilic rather than hydrophobic. In some embodiments, the hydrophilic polymer is a polymer containing —OH and/or —NH$_2$ groups. In other embodiments, the hydrophilic polymer contains ionic groups.

Suitable polymers the polymeric material may contain are polyvinyl alcohol, polyacrylate, polyacrylamide, polyacrylonitrile, polyvinyl acetate, or polyvinyl acetals.

A polymer according to the invention is a polymer containing polyvinyl alcohol or polyvinyl acetate units and acrylamide groups.

Another polymer according to the invention is a polymer containing polyvinyl alcohol or polyvinyl acetate units and acrylic acid in its protonated or deprotonated forms including counterions.

In one embodiment, the polyacrylate is a hydrolyzed polyacrylic acid ester. Examples of polyacrylates are, without limitation, sodium polyacrylate, potassium polyacrylate, ammonium polyacrylate or mixtures thereof.

The polymer material, such as PVA, can be crosslinked or not crosslinked.

In some embodiments, when a polymeric material is used that comprises a PVA-polyacrylate copolymer, the ratio of PVA units to polyacrylate units is from about 2 to 8 (about 2:8) to about 8 to 2 (about 8:2). In some embodiments, the ratio of acrylate moieties to vinylalcohol moieties is from about 2 to 8 to about 8 to 2, such as, for example in a sodium acrylate and vinyl alcohol copolymer.

When the PVA is cross-linked, the polymeric material can comprise from about 0.5% to 20% by weight of crosslinkers. The amount of crosslinkers can vary from about 0% to about 5%, about 10%, about 15%, about 20%, about 25%, about 30%, about 40%, about 50%, about 60%, about 70%, about 80%, or about 90% or higher of the polymer units.

In some embodiments, the microsphere comprises about 1% to about 95% by weight of polyvinlylalcohol. In certain embodiments, the microsphere comprises polyvinylalcohol in an amount selected from the group consisting of about 1% by weight, about 5% by weight, about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, and about 95% by weight.

In some embodiments, the hydrophilic acrylic monomer in the preparation of a PVA copolymer is selected from the group consisting of acrylamide and its derivatives, methacrylamide and its derivatives, acrylic ester acid and/or hydroxymethylmethacrylate. In some embodiments, the resulting copolymer is saponified.

Crosslinking can be carried out by using bifunctional or multifunctional monomers in the synthesis of the polymeric material. Alternatively, the polymer can also be crosslinked after its synthesis, for example, by treating the polymer (such as, for example, PVA) with an aldehyde, such as glutaraldehyde, formaldehyde, and the like. Examples of bifunctional monomers that can be used for the preparation of crosslinked copolymers, include, but are not limited to mono- or bifunctional acrylamides, e.g., the N,N'-methylene-bis-acrylamide, N',N'-diallylacryliamide or glyoxal-bis-acrylamide.

In some embodiments, the microspheres according to the invention comprise a non-ionic contrast agent. The contrast agent can be loaded on the microsphere, associated with the microsphere, absorbed by, adsorbed by or otherwise contained in or on the microsphere. Alternatively, the contrast agent is a carrier solution for the microsphere. Preferably, the contrast agent is loaded within the microsphere. In other embodiments, the microspheres do not comprise a contrast agent, such as a non-ionic contrast agent.

The non-ionic contrast agent according to the invention can be an X-ray, CT, MRI contrast agent, or a combination thereof. The contrast agent can be paramagnetic or superparamagnetic. In some embodiments, the contrast agent according to the invention is an X-ray contrast agent (also referred to as fluoroscopic agent or radio-opaque) or a CT contrast agent. In certain embodiments, the agent contains iodine. The non-ionic contrast agents can be monomeric, dimeric, or polymeric.

Examples of non-ionic contrast agents according to the invention are, without limitation, metrizamide, iopamidol (Isovue™ or Iopamiron™), iodixanol (Visipaque™) iohexol (Omnipaque™), iopromide (Ultravist™), iobtiridol, iomeprol, iopentol, iopamiron, ioxilan, iotrolan, gadodiamide, gadoteridol, iotrol, ioversol (Optiray™) or combinations thereof. In certain embodiments, the contrast agent is not iopamidol. In other embodiments, the microsphere comprises iopamidol, at least one additional non-ionic contrast agent, and/or at least one drug. In specific embodiments, non-ionic contrast agents that can be used are iodixanol, iohexal, iopromide, and ioversol. In another embodiment, the non-ionic contrast agent is gadodiamide or gadoteridol.

The microspheres according to the invention can be prepared by first synthesizing microspheres composed of the polymeric material. Examples for such microspheres are provided in, for example, EP 1 128 816 B1; WO 01/72281; JP 6-56676, JP 54-37994; and U.S. Pat. Nos. 4,320,040 and 4,367,323, which are incorporated herein by reference.

Microspheres can be prepared by suspension polymerization, drop-by-drop polymerization or any other method known to the skilled artisan. The mode of microsphere preparation selected will usually depend upon the desired characteristics, such as microsphere diameter and chemical composition, for the resulting microspheres. The microspheres of the present invention can be made by standard methods of polymerization described in the art (see, e.g., E. Boschetti, Microspheres for Biochromatography and Biomedical Applications. Part I, Preparation of Microbeads, In: *Microspheres Microencapsulation and Liposomes*, John Wiley & Sons, Arshady R., Ed., vol. 2, p. 171-189 (1999), which is incorporated herein by reference). In some embodiments, microspheres are prepared starting from an aqueous solution of monomers and optionally containing cell adhesion agents, such as collagen or gelatin (gelatin is a denatured collagen). The solution can then be mixed with a non-aqueous-compatible solvent to create a suspension of droplets, which are then turned into solid gel by polymerization of monomers by means of appropriate catalysts. Microspheres can then be collected by filtration or centrifugation, washed, and optionally sterilized. Since emulsion or suspension polymerization starts from dispersed droplets, spherical microspheres will be obtained after polymerization. The stirring speed determines the size of the droplets formed. Thus, the size of the resulting microspheres can be controlled by the stirring speed used during polymerization. In certain embodiments, the stirring speeds range from about 100 RPM to about 250 RPM, such as about 100 RPM, about 125 RPM, about 150 RPM, about 200 RPM, about 225 RPM, or about 250 RPM.

Cell adhesion promoters or marking agents can be optionally introduced on or within microspheres by chemical coupling procedures well known in affinity chromatography, referred to by the term "ligand immobilization." Another method of introduction is by diffusion within the gel network that constitutes the microsphere and then trapping the diffused molecules in place by precipitation or chemical crosslinking.

The microspheres of the invention can also be obtained by standard methods of polymerization described in the art such as French Patent 2,378,808, U.S. Pat. Nos. 5,648,100, 5,635,215 and 4,480,044, each of which is incorporated herein by reference. In general, the polymerization of monomers in solution is carried out at a temperature ranging between about 0° C. and about 100° C. and between about 40° C. and about 60° C., in the presence of a polymerization reaction initiator.

The polymerization initiator is advantageously chosen among the redox systems.

It is also possible to use combinations of an alkali metal persulfate with N,N,N',N'tetramethylethylenediamine or with dimethylaminopropionitrile, organic peroxides, such as benzoyl peroxides or 2,2'-azo-bis-isobutyronitrile. The quantity of initiator used can be adapted by one skilled in the art to the quantity of monomers and the rate of polymerization sought. Polymerization can be carried out in mass or in emulsion or suspension.

In the case of a mass polymerization, the aqueous solution containing the different dissolved constituents and the initiator undergoes polymerization in an homogeneous medium. This makes it possible to access a lump of aqueous gel which can then be separated into microspheres, by passing, for example, through the mesh of a screen.

In specific embodiments, the method of preparation is by emulsion or suspension polymerization, which makes it possible to directly access spherical microspheres of a desired size. For example, an aqueous solution containing the different dissolved constituents (e.g., different monomers and optional cell adhesion agents), can be mixed by stirring, with a liquid organic phase that is not miscible in water, and optionally in the presence of an emulsifier. The rate of stirring can be adjusted so as to obtain an aqueous phase emulsion in the organic phase forming drops of desired diameter. Polymerization can then be started by addition of the initiator. Polymerization can be accompanied by an exothermic reaction and its development can then be followed by measuring the temperature of the reaction medium.

It is possible, in some embodiments, to use as organic phase vegetable or mineral oils, certain petroleum distillation products, chlorinated hydrocarbons, or a mixture of these different solutions.

Furthermore, when the polymerization initiator includes several components (redox system), it is possible to add one of them in the aqueous phase before emulsification.

The microspheres thus obtained can then be recovered by cooling, decanting and filtration. The microspheres can then be separated by size category, for example, by using a mesh or sieve of a particular size, and washed to eliminate any trace of secondary product.

The polymerization stage can be followed by a stage of reticulation of the cell adhesion agent and possibly by a marking agent stage in the case of microspheres rendered identifiable by grafting after synthesis.

The microspheres can then optionally be contacted with a solution containing a contrast agent, such as a non-ionic contrast agent. If the microspheres are to be also loaded with a drug, the loading with the contrast agent is not carried out to complete saturation. For this purpose, the amount of liquid the microspheres can absorb is determined first. Then dry microspheres are saturated with about 10%, about 20% about 30%, about 40%, about 50%, or about 60% up to about 70% or about 80% by weight of the amount of solution that is necessary for complete saturation by the contrast agent containing solution. Then the microspheres can be loaded with a solution comprising one or more drugs or other agents to partial or complete saturation. Alternatively, the microspheres may first be loaded with a drug solution to partial or complete saturation, and subsequently (or simultaneously) loaded with a contrast agent.

As discussed elsewhere herein, it is possible to carry out the loading only to a fraction of the solution that is necessary for complete saturation and allow for complete saturation (swelling) within the tissue site for which the microspheres are intended to be implanted, injected, or otherwise administered.

Therefore, the microspheres can be administered in the methods described below already loaded with the drug, or also unloaded or only partially loaded prior, simultaneously or subsequently to the administration of the drug solution. When the microspheres and drug are administered, for example, simultaneously, separately, or in sequence, kits comprising (a) microspheres, (b) contrast agent and (c) one or more drugs are contemplated.

In specific embodiments, 100 mg of dry microspheres according to the invention can be loaded with from about 4 ml to about 12 ml, preferably about 5 ml to about 10 ml of saline solution (0.9% wt of NaCl).

Typically, the microspheres according to the invention, can be loaded with from about 1 mg to about 800 mg, about 10 mg to about 400 mg, or about 20 mg to about 300 mg of a drug per 100 mg of dry microspheres.

Typically, the microspheres can be loaded with a contrast agent, such as a nonionic contrast agent (e.g., an iodine-containing contrast agent), of from about 100 mg to about 1500 mg iodine per 100 mg of dry microspheres.

The microspheres can be loaded with from about 100 mg to about 1500 mg iodine per 100 mg of dry microspheres with an iodine-containing contrast agent and from 1 mg to about 800 mg, about 10 mg to about 400 mg, about 20 mg to about 300 mg of a drug per 100 mg dry microsphere.

The amount of loading can be determined by adding a known solution of the material to be loaded to a known amount (e.g., 100 mg) of dry microspheres. The solution is added until saturation is reached, i.e. until a supernatant is formed. The supernatant is then separated and analyzed for the amount of loading material. This amount is then subtracted from the total amount of the material used for loading to give the amount of material loaded on the microsphere.

Pharmaceutical Compositions

The invention also relates to pharmaceutical compositions comprising any of the microspheres described above and a pharmaceutically acceptable liquid or other biocompatible carrier. The compositions can be in the form of a suspension, a hydrogel, or an emulsion. The composition can also be a suspension of said microspheres in said liquid. In some embodiments, the compositions are sterile.

The pharmaceutically acceptable liquid can be, without limitation, saline, a buffer-solution, water, an isotonic solution, a biological fluid or a mixture thereof. The liquid can also be a salt solution, preferably composed of cations selected from the group consisting of sodium, potassium, calcium, magnesium, iron, zinc, and ammonium, for example, in an amount of from about 0.01 M to about 5 M.

The composition can comprise the microspheres in an amount from about 10% to about 90% by weight and the liquid (or other biocompatible carrier) in an amount from about 10% to about 90% by weight. The composition can also comprise the microspheres in an amount from about 10% to about 50% by weight and the liquid (or other biocompatible carrier) in an amount from about 50% to about 90% by weight.

In some embodiments, the biocompatible carrier is an aqueous-based solution, a hydro-organic solution, an organic solution, a non-aqueous solution, or a mixture thereof. In certain embodiments, the biocompatible carrier comprises a salt composed of cations, such as sodium, potassium, calcium, magnesium, iron, zinc, ammonium, and mixtures thereof, for example, in an amount of from about 0.01 M to about 5 M.

The compounds loaded into or onto the microspheres can be released in vivo due to physiological processes. Release of the drug or other agent loaded onto the microspheres can be influenced by pH and salt concentrations. For example, drug release can be accelerated by establishing pH changes or changes in ionic strength in the environment surrounding the microspheres. For example, drug release of doxorubicin can be released more slowly at a pH of about 7.5 than at a pH of about 5.3. Determination of such optimal drug-release conditions can easily be determined by those skilled in the art.

In some embodiments, the drug is released over a certain number of hours, days, or weeks. In one embodiment, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the drug has been released from the microsphere after a certain period of time, for example, after about 3 hours, about 6 hours, about 12 hours, about 18 hours, or after about 1 day, about 2 days, about 3 days, about 4 days, about 5 days, about 6 days, or after about 1 week, about 2 weeks, about 3 weeks, about 4 weeks, about 5 weeks, about 6 weeks, about 7 weeks, about 8 weeks, about 9 weeks, or about 10 weeks or longer. Drug release properties will depend, in part, on the properties of the specific drug used, but will be readily determinable by those skilled in the art.

In some embodiments, the drug is released from the microsphere over a certain number of days or weeks. In one embodiment more than about 1% but less than about 5% of the drug has been released within a period of about 72 hours, a period of about 96 hours, a period of within a week, a period of within two weeks, or a period of within four weeks.

In another embodiment, more than about 1% but less than about 15% of the drug has been released within a period of about 72 hours, a period of about 96 hours, a period of within a week, a period of within two weeks, and a period of within four weeks.

In yet another embodiment, more than about 1% but less than about 20% of the drug has been released within a period of about 72 hours, a period of about 96 hours, a period of within a week, a period of within two weeks, and a period of within four weeks.

In yet another embodiment, more than about 1% but less than about 25% of the drug has been released within a period of about 72 hours, a period of about 96 hours, a period of within a week, a period of within two weeks, and a period of within four weeks.

In yet another embodiment, more than about 1% but less than about 30% of the drug has been released within a period of about 72 hours, a period of about 96 hours, a period of within a week, a period of within two weeks, and a period of within four weeks.

The release as described above can be measured in vitro in the presence of 0.9% saline (NaCl solution) at room temperature (25° C.) while stirring. A typical release measurement is described in Example 5.

Methods of Treatment

The present invention provides compositions and methods suitable for treating tumors or other cancers, non-tumorigenic angiogenesis-dependent diseases, or pain, such as pain related to the presence of a tumor or other cancer. Such cancers include, without limitation, liver, ovarian, breast, kidney, lung, pancreatic, thyroid, prostate, uterine, skin cancer, head and neck tumors, breast tumors, and Kaposi's sarcoma, and superficial forms of bladder cancer. The method of treatment may be the result of localized (or systemic) drug delivery released from the drug-loaded microspheres, either alone or in combination with embolic effects of the microspheres ("active embolization"). In certain embodiments, drug-loaded microspheres of the invention are administered to a site-specific location other than a blood vessel (e.g., directly into a tumor mass), and no vessel embolization occurs.

In addition to cancer, however, numerous other non-tumorigenic angiogenesis-dependent diseases which are characterized by the abnormal growth of blood vessels can also be treated with the microspheres or pharmaceutical compositions according to the invention. Representative examples of such nontumorigenic angiogenesis-dependent diseases include, without limitation, hypertrophic scars and keloids, proliferative diabetic retinopathy, rheumatoid arthritis, arteriovenous malformations, atherosclerotic plaques, delayed wound healing, hemophilic joints, nonunion fractures, Osier-Weber syndrome, psoriasis, pyogenic granuloma, scleroderma, tracoma, menorrhagia and vascular adhesions.

Similarly, the microspheres and compositions of the invention can be used to deliver drugs to various cells, tissues or organs in need thereof. For example, the microspheres and compositions can be used to treat tumors or cancers, inflammatory diseases or other diseases associated with inflammation, or symptoms thereof.

It should be understood that the patients suitable for passive embolization, active embolization or drug delivery with the microspheres according to the invention include humans and animals, preferably humans including male and female infants, children, and adults, including the elderly. Patients at risk for, or currently afflicted with, hepatocellular diseases, such as hepatitis or liver cancer, are a particularly preferred patient population, for example Caucasian or Asian (e.g., including, but not limited to, people of Japanese heritage) human patients, 18 to 75 years of age. In some embodiments, the patients are 25-75, 25-50, 50-75, or 18-25 years of age. In one embodiment, the patient is less than 18 years of age (e.g., 1-5, 5-10, 10-15, 15-18 years of age). In another embodiment, the patient is older than 75 years of age.

In some embodiments, the microspheres of the invention are used in the treatment, management, or prevention of hepatocellular disease in a patient. In one embodiment, the patient is Child-Pugh class A. In another embodiment, the patient is Child-Pugh class B. In yet other embodiments, the patient is Child-Pugh class C. The Child-Pugh classification is well known in the art, see, e.g., Child and Turcotte (1964) Surgery and portal hypertension, In: The liver and portal hypertension (Edited by: Child CG). Philadelphia, Saunders 1964, 50-64; which was later modified by Pugh et al. Transection of the esophagus in bleeding oesophageal varices (1973) *Br. J. Surg.* 60:648-652. In some embodiments, the patient is infected with Hepatitis C virus.

The microspheres and pharmaceutical compositions according to the invention can be used in passive embolization therapies and in active embolization therapies. The microspheres can also be used as delivery systems, e.g., as drug-delivery systems, with or without embolization.

The microspheres can contain a contrast agent, such as a non-ionic contrast agent, and at least one (e.g., one, two, three, four or more) drug(s) or other agent(s). Such a drug can be any one or more of an anti-neoplastic drug, anti-angiogenesis drug, anti-fungal drug, anti-viral drug, anti-inflammatory drug, anti-bacterial drug, a cytotoxic drug, a chemotherapeutic or pain relieving drug and/or an anti-histamine drug. The drug may also be, for example, any one or more of hormones, steroids, vitamins, cytokines, chemokines, growth factors, interleukins, enzymes, anti-allergenic agents, circulatory drugs, anti-tubercular agents, anti-anginal agents, anti-protozoan agents, anti-rheumatic agents, narcotics, cardiac glycoside agents, sedatives, local anesthetic agents, general anesthetic agents, and combinations thereof. When used for the treatment of pain, the microspheres according to the invention are preferably loaded with a pain relieving drug.

In one embodiment, the microsphere comprises an anti-angiogenic or anti-neoplastic drug. In another embodiment, the microsphere comprises a chemotherapeutic or pain relieving drug. In some embodiments, the microsphere comprises one or more anti-neoplastic drugs and one or more chemotherapeutic or pain relieving drugs.

Examples of anti-angiogenic or anti-neoplastic drugs include, without limitation, alkylating agents, nitrogen mustards, antimetabolites, gonadotropin releasing hormone antagonists, androgens, antiandrogens, antiestrogens, estrogens, and combinations thereof. Specific examples include but are not limited to actinomycin D, aldesleukin, alemtuzumab, alitretinoin, allopurinol, altretamine, amifostine, aminoglutehimide, amphotercin B, amsacrine, anastrozole, ansamitocin, arabinosyl adenine, arsenic trioxide, asparaginase, aspariginase *Erwinia*, BCG Live, benzamide, bevacizumab, bexarotene, bleomycin, 3-bromopyruvate, busulfan, calusterone, capecitabine, carboplatin, carzelesin, carmustine, celecoxib, chlorambucil, cisplatin, cladribine, cyclophosphamide, cytarabine, cytosine arabinoside, dacarbazine, dactinomycin, darbepoetin alfa, daunorubicin, daunomycin, denileukin diftitox, dexrazoxane, dexamethosone, docetaxel, doxorubicin, dromostanolone, epirubicin, epoetin alfa, estramustine, estramustine, etoposide, VP-16, exemestane, filgrastim, floxuridine, fludarabine, fluorouracil (5-FU), flutamide, fulvestrant, demcitabine, gemcitabine, gemtuzumab, goserelin acetate, hydroxyurea, ibritumomab, idarubicin, ifosfamide, imatinib, interferon (e.g., interferon α-2a, interferon α-2b), irinotecan, letrozole, leucovorin, leuprolide, lomustine, meciorthamine, megestrol, melphalan (e.g., PAM, L-PAM or phenylalanine mustard), mercaptopurine, mercaptopolylysine, mesna, mesylate, methotrexate, methoxsalen, mithramycin, mitomycin, mitotane, mitoxantrone, nandrolone phenpropionate, nolvadex, oprelvekin, oxaliplatin, paclitaxel, pamidronate sodium, pegademase, pegaspargase, pegfilgrastim, pentostatin, pipobroman, plicamycin, porfimer sodium, procarbazine, quinacrine, raltitrexed, rasburicase, riboside, rituximab, sargramostim, spiroplatin, streptozocin, tamoxifen, tegafur-uracil, temozolomide, teniposide, testolactone, tioguanine, thiotepa, tissue plasminogen activator, topotecan, toremifene, tositumomab, trastuzumab, treosulfan, tretinoin, trilostane valrubicin, vinblastine, vincristine, vindesine, vinorelbine, zoledronate, salts thereof, or mixtures thereof.

In some embodiments, the platinum compound is spiroplatin, cisplatin, or carboplatin. In specific embodiments, the drug is cisplatin, mitomycin, paclitaxel, tamoxifen, doxorubicin, tamoxifen, or mixtures thereof.

Other anti-angiogenic or anti-neoplastic drugs include, but are not limited to AGM-1470 (TNP-470), angiostatic steroids, angiostatin, antibodies against αvβ3, antibodies against bFGF, antibodies against IL-1, antibodies against TNF-α, antibodies against VEGF, auranofin, azathioprine, BB-94 and BB-2516, basic FGF-soluble receptor, carboxyamido-trizole (CAI), cartilage-derived inhibitor (CU), chitin, chloroquine, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, Glioma-derived angiogenesis inhibitory factor (GD-AIF), GM 1474, gold chloride, gold thiomalate, heparinases, hyaluronan (high and low molecular-weight species), hydrocortisonelbeta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, martmastat (BB-2516), medroxyprogesterone, methotrexate, minocycline, nitric oxide, octreotide (somatostatin analogue), D-penicillamine, pentosan polysulfate, placental proliferin-related protein, placental RNase inhibitor, plasminogen activator inhibitor (PAIs), platelet factor-4 (PF4), prednisolone, prolactin (16-kDa fragment), proliferin-related protein, prostaglandin synthase inhibitor, protamine, retinoids, somatostatin, substance P, suramin, SU1O1, tecogalan sodium (05-4152), tetrahydrocortisolsthrombospondins (TSPS), tissue inhibitor of metalloproteinases (TIMP 1, 2, 3), thalidomide, 3-aminothalidomide, 3-hydroxythalidomide, metabolites or hydrolysis products of thalidomide, 3-aminothalidomide, 3-hydroxythalidomide, vitamin A and vitreous fluids. In another preferred embodiment, the anti-angiogenic agent is selected from the group consisting of thalidomide, 3-aminothalidomide, 3-hydroxythalidomide and metabolites or hydrolysis products of thalidomide, 3-aminothalidomide, 3-hydroxythalidomide. In a preferred embodiment, the anti-angiogenic agent is thalidomide. The above anti-angiogenic agents are disclosed in U.S. Pat. Nos. 5,593,990; 5,629,327; and 5,712,291; Norrby, APMIS, 1997, 105:417-437; O'Reilly, *Investigational New Drugs,* 1997, 15:5-13; and *J. Nat'l Cancer Instit.,* 1996, 88(12):786-788, the contents of which are incorporated herein by reference.

Examples of pain reliving drugs are, without limitation, analgesics or anti-inflammatories, such as non-steroidal anti-inflammatory drugs (NSAID), ibuprofen, ketoprofen, dexketoprofen, phenyltoloxamine, chlorpheniramine, furbiprofen, vioxx, celebrex, bexxstar, nabumetone, aspirin, codeine, codeine phosphate, acetaminophen, paracetamol, xylocalne, and naproxin.

In some embodiments, the pain relieving drug is an opioid. Opioids are commonly prescribed because of their effective analgesic, or pain relieving, properties. Among the compounds that fall within this class include narcotics, such as morphine, codeine, and related medications. Other examples of opioids include oxycodone, propoxyphene, hydrocodone, hydromorphone, and meperidine.

Other compounds, drugs, or other agents for which the microspheres according to the invention can be used as delivery systems, either with or without embolization, are listed, without limitation, below.

Blood Products

Blood products, include, for example, without limitation, erythropoietin, parenteral iron, hemin, and hematoporphyrins and their derivatives.

Biological Response Modifiers

Biological response modifiers, include, for example, without limitation, muramyldipeptide, muramyltripeptide, lymphokines (e.g., bacterial endotoxin such as lipopolysaccharide, macrophage activation factor), sub-units of bacteria (such as *Mycobacteria, Corynebacteria*), the synthetic peptide, N-acetyl-muramyl-L-alanyl-Disoglutamine, and prostaglandins.

Anti-Fungal Agents

Anti-fungal agents, include, for example, without limitation, ketoconazole, nystatin, griseofulvin, flucytosine (5-fc), miconazole, amphotericin B, ricin, and β-lactam antibiotics (e.g., sulfazecin).

Hormones and Steroids

Hormones and steroids, include, for example, without limitation, growth hormone, melanocyte stimulating hormone, adrenocortiotropic hormone, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolonehexacetonide, triamcinolone acetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisoneacetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosteroneenanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, flunisolide, hydrocortisone sodium succinate, methylprednisolone sodium succinate, prednisolone phosphate sodium, triamcinolone acetonide, hydroxydione sodium spironolactone, oxandrolone, oxymetholone, prometholone, testosterone cypionate, testosterone phenylacetate, estradiol cypionate, and norethynodrel.

Vitamins

Vitamins, include, for example, without limitation, cyanocobalamin neinoic acid, retinoids and derivatives thereof such as retinol palmitate, alpha-tocopherol, naphthoquinone, cholecalciferol, folic acid and tetrahydrofolate.

Peptides and Peptide Analogs

Peptides and peptide analogs, include, for example, without limitation, manganese super oxide dismutase, tissue plasminogen activator (t-PA), glutathione, insulin, dopamine, peptide ligands containing RGD, AGD, RGE, KGD, KGE or KQAGDV (peptides with affinity for theGPEXma receptor), opiate peptides, enkephalins, endorphins and their analogs, human chorionicgonadotropin (HCG), corticotropin release factor (CRF), cholecystokinins and their analogs, bradykinins and their analogs and promoters and inhibitors, elastins, vasopressins, pepsins, glucagon, substance P, integrins, captopril, enalapril, lisinopril and other ACE inhibitors, adrenocorticotropic hormone (ACTH), oxytocin, calcitonins, IgG or fragments thereof, IgA or fragments thereof, IgM or fragments thereof, ligands for Effector Cell Protease Receptors (all subtypes), thrombin, streptokinase, urokinase, t-PA and all active fragments or analogs, Protein Kinase C and its binding ligands, interferons (α-IFN, β-IFN, γ-IFN), colony stimulating factors (CSF), granulocyte colony stimulating factors (GCSF), granulocyte-macrophage colony stimulating factors (GM-CSF), tumor necrosis factors (TNF), nerve growth factors (NGF), platelet derived growth factors, lymphotoxin, epidermal growth factors, fibroblast growth factors, vascular endothelial cell growth factors, erythropoietin, transforming growth factors, oncostatin M, interleukins (IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, etc.), metalloprotein kinase ligands, collagenases and agonists and antagonists.

Antibodies

Antibodies, include, for example, without limitation, substantially purified antibodies or fragments thereof, including non-human antibodies or fragments thereof. In various embodiments, the substantially purified antibodies or fragments thereof, can be human, non-human, chimeric and/or humanized antibodies. Such non-human antibodies can be goat, mouse, sheep, horse, chicken, rabbit, or rat antibodies. Alternatively, the non-human antibodies of the invention can be chimeric and/or humanized antibodies. Completely human antibodies are particularly desirable for therapeutic treatment of human patients. A chimeric antibody is a molecule in which different portions are derived from different animal species, such as those having a variable region derived from a murine monoclonal antibody (mAb) and a human immunoglobulin constant region (Cabilly et al., U.S. Pat. No. 4,816,567; and Boss et al., U.S. Pat. No. 4,816,397, which are incorporated herein by reference in their entirety.). In addition, the non-human antibodies could be polyclonal antibodies or monoclonal antibodies. Any of the antibodies used with the microspheres of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material. The term "monoclonal antibody" or "monoclonal antibody composition," as used herein, refers to a population of antibody molecules that contain only one species of an antigen binding site capable of immunoreacting with a particular epitope. Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of, for example, a receptor on the surface of a cancer cell of a tumor to be treated by the compositions of the present invention.

Anti-Mitotic Factors

Anti-mitotic factors include, without limitation, estramustine and its phosphorylated derivative, estramustine-phosphate, doxorubicin, amphethinile, combretastatin A4, and colchicine.

Vaccines

Vaccines include, for example, without limitation, pneumococcus vaccine, poliomyelitis vaccine, anthrax vaccine, tuberculosis (BCG) vaccine, hepatitis A vaccine, cholera vaccine, meningococcus A, C, Y vaccines, W135 vaccine, plague vaccine, rabies (human diploid) vaccine, yellow fever vaccine, Japanese encephalitis vaccine, typhoid (phenol and heat-killed) vaccine, hepatitis B vaccine, diphtheria vaccine, tetanus vaccine, pertussis vaccine, *H. influenzae* type b vaccine, polio vaccine, measles vaccine, mumps vaccine, rubella vaccine, varicella vaccine, *streptococcus pneumoniae* Ty (live mutant bacteria) vaccine, Vi (Vi capsular polysaccharide) vaccine, DT (toxoid) vaccine, Td (toxoid) vaccine, aP (inactive bacterial antigen/accelular (DtaP)) vaccine, Hib (bacterial polysaccharide-protein conjugate) vaccine, hepatitis B virus (inactive serum derived viral antigen/recombinant antigen) vaccine, influenza vaccine, rotavirus vaccine, respiratory syncytial virus (RSV) vaccine, human astrovirus vaccine, rotavirus vaccine, human influenza A and B virus vaccine, hepatitis A virus vaccine, live attenuated parainfluenza virus type 3 vaccine, enterovirus vaccines, retrovirus vaccines, and picomavirus vaccines.

Anti-Allergenic Agents

Anti-allergenic agents, include, for example, without limitation, amelexanox.

Anti-Coagulation Agents

Anti-coagulation agents, include, for example, without limitation, phenprocoumon and heparin.

Circulatory Drugs

Circulatory drugs, include, for example, without limitation, propranolol.

Anti-Tubercular Agents

Anti-tubercular agents, include, for example, without limitation, para-aminosalicylic acid, isoniazid, capreomycin sulfatecycloserine, ethambutol hydrochloride ethionamide, pyrazinamide, rifampin, and streptomycin sulfate.

Anti-Viral Agents

Anti-viral agents, include, for example, without limitation, acyclovir, amantadine azidothymidine (AZT or Zidovudine), ribavirin, and vidarabine monohydrate (adenine arabinoside, ara-A).

Anti-Anginal Agents

Anti-anginal agents, include, for example, without limitation, diltiazem, nifedipine, verapamil, erythritol tetranitrate, isosorbide dinitrate, nitroglycerin (glyceryl trinitrate), and pentaerythritolteiranitrate.

Antibiotics

Antibiotics, include, for example, dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, and tetracycline.

Anti-Inflammatory Agents and Analgesics

Anti-inflammatory agents and analgesics, include, for example, diflunisal, ibuprofen, indomethacin, meclofenamate, mefenamic acid, naproxen, oxyphenbutazone, phenylbutazone, piroxicam, sulindac, tolmetin, aspirin and salicylates.

Anti-Protozoan Agents

Anti-prozoan agents, include, for example, without limitation, chloroquine, metronidazole, hydroxychloroquine, quinine, andmeglumine antimonate.

Anti-Rheumatic Agents

Anti-rheumatic agents, include, for example, without limitation, penicillamine.

Narcotics

Narcotics, include, for example, without limitation, paregoric and opiates, such as codeine, heroin, methadone, morphine and opium.

Cardiac Glycoside Agents

Cardiac glycoside agents, include, for example, without limitation, deslanoside, digitoxin, digoxin, digitalin and digitalis.

Neuromuscular Blocking Agents

Neuromuscular blocking agents, include, for example, without limitation, atracurium mesylate, gallamine triethiodide, hexafluorenium bromide, metocurine iodide, pancuronium bromide, succinylcholine chloride (suxamethonium chloride), tubocurarine chloride, and vecuronium bromide.

Sedatives (Hypnotics)

Sedatives, include, for example, without limitation, amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride paraldehyde, pentobarbital, pentobarbital sodium, phenobarbital sodium, secobarbital sodium, talbutal, temazepam, and triazolam.

Local Anesthetic Agents

Local anesthetic agents, include, for example, without limitation, bupivacaine hydrochloride, chloroprocaine hydrochloride, etidocaine hydrochloride, lidocaine hydrochloride, mepivacaine hydrochloride, procaine hydrochloride, and tetracaine hydrochloride.

General Anesthetic Agents

General anesthetic agents, include, for example, without limitation, droperidol, etomidate, fentanyl citrate with droperidol, ketamine hydrochloride, methohexital sodium, and thiopental sodium.

Radioactive Particles or Ions

Radioactive particles or ions, include, for example, without limitation, strontium, rhenium, yttrium, technetium, and cobalt.

Cell-Adhesion Promoters

In some embodiments, the microspheres can comprise a cell adhesion promoter. Various types of cell adhesion promoters well known in the art can be used in the present invention. In particular, cell adhesion promoters can be selected from collagen, gelatin, glucosaminoglycans, fibronectins, lectins, polycations (such polylysine, chitosan and the like), or any other natural or synthetic biological cell adhesion agent. Preferably, the cell adhesion promoter is present in the microsphere, or other solid substrate, in an amount between about 0.1 to 1 g per ml of settled microspheres.

The targeting aspects of the invention further enable lowered dosages to be applied for therapy, since the effective concentration at the therapeutic site remains undiluted in the body. The amount of the drug or agent of the present invention to be administered to a patient depends, for example, on the particular drug or agent that is used, the method in which the drug/agent is being administered, and the age, sex, weight and physical condition of the patient. Generally, treatment is initiated with small dosages, which can then be increased by small increments, until the desired effect under the circumstances is achieved. Additionally, one skilled in the art can rely on reference materials, such as the *Physician's Desk Reference*, published by Medical Economics Company at Montvale, N.J., to determine the appropriate amount of a particular drugs/agents, and hence such a dose or a lower or higher dose can be administered to a patient using the methods of the present invention. In accordance with the present invention, the prodrug is delivered to the patient (e.g., in a region of the patient) for the purposes, for example, of treating a condition (i.e., a disease state, malady, disorder, etc.) in the patient. The prodrugs can be used as above or can be incorporated into other embodiments, such as emulsions.

Diseases contemplated for treatment with the compositions and methods of the present invention include, for example, without limitation, tumors associated with the liver, kidney, acute lymphoblastic leukemia, acute myeloid leukemia, Ewing's sarcoma, gestational trophoblastic carcinoma, Hodgkin's disease, non-Hodgkin's lymphoma, Burkitt's lymphoma diffuse large cell lymphoma, follicular mixed lymphoma, lymphoblastic lymphoma, rhabdomyosarcoma, testicular carcinoma, Wilms's tumor, anal carcinoma, bladder carcinoma, breast carcinoma, chronic lymphocytic leukemia, chronic myelogenous leukemia, hairy cell leukemia, head and neck carcinoma, meningioma, neuro fibrosoma, angio fibrosoma, lung (small cell) carcinoma, multiple myeloma, Non-Hodgkin's lymphoma, follicular lymphoma, ovarian carcinoma, brain tumors (astrocytoma), cervical carcinoma, colorectal carcinoma, hepatocellular carcinoma, human large hepatocellular carcinoma, Kaposi's sarcoma, lung (non-small-cell) carcinoma, melanoma, pancreatic carcinoma, prostate carcinoma, soft tissue sarcoma, breast carcinoma, colorectal carcinoma (stage II), bone tumors, osteogenic sarcoma, ovarian carcinoma, uterine fibroids, testicular carcinoma, or combinations thereof.

Embolization therapy and/or drug delivery of the present invention may be utilized in at least three principal ways to assist in the management or treatment of neoplasms: (1) definitive treatment of tumors (usually benign); (2) for pre-operative embolization; and (3) for palliative embolization. Briefly, benign tumors may sometimes be successfully treated by embolization therapy alone. Examples of such tumors include simple tumors of vascular origin (e.g., haemangiomas), endocrine tumors such as parathyroid adenomas, and benign bone tumors.

For other tumors, (e.g., renal adenocarcinoma), preoperative embolization and/or drug delivery may be employed hours or days before surgical resection in order to reduce operative blood loss, shorten the duration of the operation, and reduce the risk of dissemination of viable malignant cells by surgical manipulation of the tumor. Many tumors may be successfully embolized and/or drugs can be delivered preoperatively, including for example nasopharyngeal tumors, glomus jugular tumors, meningiomas, chemodectomas, and vagal neuromas.

It should be evident that a wide variety of tumors may be treated, such as by embolization and/or by drug-delivery, using the methods and compositions of the present invention. Briefly, tumors are typically divided into two classes: benign and malignant. In a benign tumor the cells retain their differentiated features and do not divide in a completely uncontrolled manner. In addition, the tumor is localized and non-metastatic. In a malignant tumor, the cells become undifferentiated, do not respond to the body's growth and hormonal signals, and multiply in an uncontrolled manner; the tumor is invasive and capable of spreading to distant sites (metastasizing).

Within one aspect of the present invention, metastases (secondary tumors) of the liver may be treated utilizing the compositions and methods of the present invention by embolization therapy and/or drug delivery. Briefly, a catheter can be inserted via the femoral or brachial artery and advanced into the hepatic artery by steering it through the arterial system under fluoroscopic guidance. The catheter can be advanced into the hepatic arterial tree as far as necessary to allow complete blockage of the blood vessels supplying the tumor(s), while sparing as many of the arterial branches supplying normal structures as possible. In certain embodiments, this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery can be embolized by injecting anti-angiogenic therapeutic compositions through the arterial catheter until flow in the artery to be blocked ceases, preferably even after observation for 5 minutes. Occlusion of the artery may be confirmed by injecting radiopaque contrast through the catheter and demonstrating by fluoroscopy or X-ray film that the vessel which previously filled with contrast no longer does so. The same procedure may be repeated with each feeding artery to be occluded.

Within another aspect of the present-invention, active therapeutic embolization therapy can be used during surgery to remove a tumor or vascular mass or cancerous organ. Additionally, another aspect of the present invention concerns the use of active therapeutic embolization therapy to prevent or ameliorate metastasis.

As noted above, both benign and malignant tumors can be targets of the compositions and methods of the present invention. Representative examples of benign hepatic tumors include hepatocellular adenoma, cavernous haemangioma, and focal nodular hyperplasia. Other benign tumors, which are more rare and often do not have clinical manifestations, may also be treated. These include bile duct adenomas, bile duct cystadenomas, fibromas, lipomas, leiomyomas, mesotheliomas, teratomas, myxomas, and nodular regenerative hyperplasia.

Malignant hepatic tumors are generally subdivided into two categories: primary and secondary. Primary tumors arise directly from the tissue in which they are found. Thus, a primary liver tumor is derived originally from the cells which make up the liver tissue (such as hepatocytes and biliary cells). Representative examples of primary hepatic malignancies which may be treated by arterial embolization include hepatocellularcarcinoma, cholangiocarcinoma, angiosarcoma, cystadenocarcinoma, squamous cell carcinoma, and hepatoblastoma.

A secondary tumor, or metastasis, is a tumor which originated elsewhere in the body but has subsequently spread to a distant organ. The common routes for metastasis are direct growth into adjacent structures, spread through the vascular or lymphatic systems, and tracking along tissue planes and body spaces (peritoneal fluid, cerebrospinal fluid, etc.). Secondary hepatic tumors are one of the most common causes of death in the cancer patient and are by far and away the most common form of liver tumor. Although virtually any malignancy can metastasize to the liver, tumors which are most likely to spread to the liver include: cancer of the stomach, colon, and pancreas; melanoma; tumors of the lung, oropharynx, and bladder; Hodgkin's and non-Hodgkin's lymphoma; tumors of the breast, ovary, and prostate. Each one of the above-named primary tumors has numerous different tumor types which may be treated by arterial embolization (for example, without limitation, there are reportedly over 32 different types of ovarian cancer).

Methods of Administration

The diseases or disorders above can be treated or prevented by administering to the mammal in need thereof a therapeutically effective amount of the microspheres or a pharmaceutical composition according to the invention. The microspheres can be administered in their completely swollen state or also in a partially swollen state.

Administration is typically carried out by injection. In certain embodiments, the microspheres are administered by a catheter. In other embodiments, the microspheres are injected us a needle attached to a syringe. In some embodiments, administration is into a blood vessel. In other embodiments, administration is directly to the site of action, for example into a tumor mass, or into a cell, organ or tissue requiring such treatment. The microspheres according to the invention can be administered already loaded with a drug. In other embodiments, the microspheres are administered in combination with a drug solution, wherein the drug solution is administered prior, simultaneously or after the administration of the microspheres.

When administered, the microspheres or the pharmaceutical composition are suitable for injection. In specific embodiments, the microspheres or compositions comprising the microspheres are sterile.

Kits

The invention further relates to pharmaceutical packs and kits comprising one or more containers filled with one or more of the ingredients of the aforementioned compositions of the invention. The kits can comprise microspheres, a contrast agent, and solution comprising one or more drugs, wherein one, two, three or more of the components can be in one, two, three or more vials. Associated with such container(s) can be a notice in the form prescribed by a governmental agency regulating the manufacture, use or sale of pharmaceuticals or biological products, reflecting approval by the agency of the manufacture, use or sale of the product for patient (e.g., human or other mammal) administration. The reagents of any of the assays or methods described herein can also be included as components of a kit.

In one kit format, the microspheres of the present invention are present in a liquid, physiologically compatible solution in one vial. In another kit format, the microspheres of the present invention can be provided in dry form in one vial and the drug solution and contrast agent can be provided in a second and/or optionally a third vial. In certain embodiments, the microsphere comprising the contrast agent are present in one vial, and the drug is present in solution in another vial. In this form, the contents of the two vials can be mixed together prior to or concurrently with administration. In other embodiments, the microspheres comprising the contrast agent and the drug are provided in dry form in one vial. The powder can then be suspended in a suitable liquid prior to administration or a second vial is provided, which contains the injectable solution and the contents of both vials are combined prior to administration or concurrently with administration.

Finally, in another kit format the microspheres of the present invention are present in one vial and a second vial contains a pharmaceutically acceptable solution comprising the contrast agent. The microspheres in the first vial can be pre-loaded with a drug, or the drug solution can optionally be present in a third vial. The microspheres can then be mixed together with the drug solution and/or contrast agent, for example, prior to or concurrently with administration.

The following examples are offered by way of illustration, and not by way of limitation.

Example 1

Preparation of Microspheres

One-half of a gram of benzoyl peroxide as a polymerization initiator is added to 60 g of vinyl acetate and 40 g of methyl acrylate. This is dispersed in 300 ml of water containing 3 g of partially saponified polyvinylalcohol as a dispersion stabilizer and 10 g of NaCl. The suspension polymerization is carried at 65° C. for 6 hours. After removing the solvent, the polymer is dried for 24 hours in a freeze dryer. Twenty grams of the dried powder is suspended in a saponification fluid containing 200 g of methanol and 10 g of water. Then 40 ml of 10 N NaOH solution was added drop wise by maintaining the reaction at 10° C., and then the reaction was carried out at 30° C. for 24 hours. After the saponification reaction is completed, the reaction product is washed with methanol, after which 15.8 g of spherical dry saponified product with a particle diameter of about 50 µm to about 240 µm is obtained after drying. The product is then sieved and calibrated into, e.g., about 50 µm increments, to get several size ranges, e.g., about 50 µm-100 µm, about 100 µm-150 µm, about 150 µm-210 µm. The sieved products can then be lyophilized.

Example 2

Preparation of Microspheres with Non-Ionic Contrast Agent

One hundred milligrams of dry microspheres obtained as described above in Example 1 are added to 10 ml of a iodixanol solution (e.g., Visipaque™, Nycomed, 320 mg iodine/ml), and about 1 ml of supernatant remains.

The (wet) microspheres can be sterilized, for example, by irradiation and are then ready for use. Alternatively, the microspheres can be lyophilized and stored.

Example 3

Preparation of Drug-Loaded Microspheres with Non-Ionic Contrast Agent

To the 100 mg of microspheres obtained in Example 1 are added 5 ml of a doxorubicin solution (e.g., Adriamycin™, 2 mg/ml), and the solution is completely absorbed. Then 5 ml of a iodixanol solution (e.g., Visipaque™, Amersham, 320 mg/ml iodine) is added. About 1 ml of clear supernatant remains.

The microspheres can optionally be sterilized and used for injection into a patient.

Example 4

Preparation of Drug-Loaded Microspheres with Contrast Agent

To compare the swellability, compressibility and loading capacity of drug-loaded PVA-containing microspheres with non-ionic versus ionic contrast media, the following experiment can be performed. While this experiment uses an ionic contrast agent, a parallel experiment can also be run using a non-ionic contrast agent (see, e.g., Example 5).

One hundred micrograms of the microspheres obtained in Example 1 are added to 5 ml of a doxorubicin solution (e.g., Adriamycin™, 2 mg/ml) and the solution is completely absorbed. Then 5 ml of a ioxaglate (e.g., Hexabrix®), Mallinckrodt, 320 mg/ml of iodine) solution is added. The supernatant shows the red color of the doxorubicin solution, showing that doxorubicin leaked from the microspheres after addition of ionic contrast agent.

A comparison of the results of drug-loaded microspheres in the presence of ionic versus non-ionic contrast agent will show that PVA-containing microspheres comprising a non-ionic contrast agent have increased loading capacity as compared to those comprising ionic contrast agents. For example, in some instances, microspheres plus human serum (e.g., 5 ml) and ionic contrast agent (50/50) results in a swelling rate of about 3.9, whereas the same mixture with a non-ionic contrast agent results in a swelling rate of about 4.8 (123%).

Example 5

Comparative Drug Release

A typical release experiment can be performed as follows:

A solution of doxorubicin hydrochloride (50 mg in 5 ml of saline from Haorui Pharma Chem, Inc.) was added to 100 mg of dry microspheres prepared as described in Example 1. Microspheres of a size range from 50 μm to 100 μm were used. After 25 minutes, 5 ml of contrast agent was added. Two different contrast agents were used in separate experiments: Hexabrix 320® (ionic contrast agent) and Visipaque 320% (non-ionic contrast agent). The microsphere suspension was then transferred into a 10 ml dialysis membrane (Spectrapor®, MW 100,000) without removal of supernatant and the dialysis membrane was sealed.

The dialysis membrane was placed in a graded cylinder filled with a solution of 450 ml saline (0.9% wt. NaCl) and 50 ml methanol. The stir bar was added to the cylinder, and the stirring speed was set to low. Samples of 150 μl were taken at different time intervals and examined for the concentration of doxorubicin. The concentration of doxorubicin in the samples was measured by HPLC (Waters, Interchrom column Uptisphere, UV detection at 480 nm).

The experiments showed that after 72 hours about 0.8% wt of the originally present doxorubicin had been released from the microspheres loaded with the non-ionic contrast agent, while 3.0% doxorubicin was released from the microspheres containing the ionic contrast agent.

The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "a drug" includes a mixture of two or more such drugs, reference to "a microsphere" includes mixtures of two or more such microspheres, and the like. Additionally, ordinarily skilled artisans will recognize that operational sequences must be set forth in some specific order for the purpose of explanation and claiming, but the present invention contemplates various changes beyond such specific order.

The contents of all references described herein are hereby incorporated by reference.

Other embodiments are within the following claims.

What is claimed is:

1. A substantially spherical microsphere comprising:
   a biocompatible polymeric material comprising polyvinylalcohol,
   doxorubicin in a concentration of about 10 mg to about 400 mg of doxorubicin per 100 mg of dry microspheres, and
   a non-ionic contrast agent in a concentration of about 100 mg to about 3200 mg iodine per 100 mg of dry microspheres, wherein the non-ionic contrast agent is selected from at least one of the following: metrizamide, iopamidol, iodixanol, iohexol, ioversol, iopromide, iobitridol, iomeprol, iopentol, iopamiron, ioxilan, iotrolan, iotrol, ioversol, and combinations thereof,
   wherein the microsphere is swellable in a pharmaceutically acceptable solution and has a diameter of from about 10 μm to about 1000 μm before swelling, wherein the diameter of the microsphere is from about 40 μm to about 2000 μm after swelling, and wherein more than 1% but less than 20% of the loaded doxorubicin is configured to be released from within the microsphere within a period of 72 hours.

2. The microsphere of claim 1, wherein the non-ionic contrast agent is selected from at least one of the following: X-ray, CT, paramagnetic and superparamagnetic contrast agents.

3. The microsphere of claim 1, wherein the microsphere comprises about 1% to about 95% by weight of polyvinylalcohol.

4. The microsphere of claim 1, wherein the polyvinylalcohol is cross-linked.

5. The microsphere of claim 1, wherein the polyvinylalcohol comprises a copolymer of polyvinylalcohol.

6. The microsphere of claim 1, wherein the polymeric material further comprises an ionic group.

7. The microsphere of claim 1, wherein the polymeric material can absorb at least 5% by weight of water.

8. The microsphere of claim 1, wherein the polymeric material has a water absorption rate between about 300 and about 750 gm/gm of dry weight.

9. The microsphere of claim 1, wherein the concentration of non-ionic contrast agent is from about 100 mg to about 1500 mg iodine per 100 mg of dry microspheres.

10. A substantially spherical microsphere comprising:
    a biocompatible polymeric material comprising polyvinylalcohol,
    a drug selected from at least one of the following: daunorubicin, daunomycin, doxorubicin, irinotecan and topotecan, wherein the concentration of the drug is about 10 mg to about 400 mg of drug per 100 mg of dry microspheres, and a non-ionic contrast agent in a concentration of about 100 mg to about 3200 mg iodine per 100 mg of dry microspheres, wherein the non-ionic contrast agent is selected from at least one of the following: metrizamide, iopamidol, iodixanol, iohexol, ioversol, iopromide, iobitridol, iomeprol, iopentol, iopamiron, ioxilan, iotrolan, iotrol, ioversol, and combinations thereof, wherein the microsphere is swellable in a pharmaceutically acceptable solution and has a diameter of from about 10 μm to about 1000 μm before swelling, wherein the diameter of the microsphere is from about 40 μm to about 2000 μm after swelling, and wherein more than 1% but less than 20% of the loaded drug is configured to be released from within the microsphere within a period of 72 hours.

11. The microsphere of claim 10, wherein the microsphere comprises about 1% to about 95% by weight of polyvinylalcohol.

12. The microsphere of claim 10, wherein the polyvinylalcohol is cross-linked.

13. The microsphere of claim 10, wherein the polyvinylalcohol comprises a copolymer of polyvinylalcohol.

14. The microsphere of claim 10, wherein the polymeric material further comprises an ionic group.

15. The microsphere of claim 10, wherein the concentration of non-ionic contrast agent is from about 100 mg to about 1500 mg iodine per 100 mg of dry microspheres.

* * * * *